US010626108B2

United States Patent
Jonckers et al.

(10) Patent No.: US 10,626,108 B2
(45) Date of Patent: Apr. 21, 2020

(54) HETEROCYCLIC INDOLES FOR USE IN INFLUENZA VIRUS INFECTION

(71) Applicant: Janssen Sciences Ireland UC, County Cork (IE)

(72) Inventors: Tim Hugo Maria Jonckers, Heist op den Berg (BE); David Craig McGowan, Brussels (BE); Jérôme Émile Georges Guilllemont, Andé (FR); Ludwig Paul Cooymans, Beerse (BE); Werner Constant Johan Embrechts, Beerse (BE); Christophe Francis Robert Nestor Buyck, Hamme (BE); Wendy Mia Albert Balemans, Kalmthout (BE); Pierre Jean-Marie Bernard Raboisson, Rosieres (BE)

(73) Assignee: JANSSEN SCIENCES IRELAND UC, County Cork (IE)

( * ) Notice: Subject to any disclaimer, the term of this patent is extended or adjusted under 35 U.S.C. 154(b) by 0 days.

(21) Appl. No.: 15/779,468

(22) PCT Filed: Nov. 25, 2016

(86) PCT No.: PCT/EP2016/078778
§ 371 (c)(1),
(2) Date: May 25, 2018

(87) PCT Pub. No.: WO2017/089518
PCT Pub. Date: Jun. 1, 2017

(65) Prior Publication Data
US 2018/0258074 A1  Sep. 13, 2018

(30) Foreign Application Priority Data
Nov. 27, 2015  (EP) .................................... 15196811

(51) Int. Cl.
| C07D 403/04 | (2006.01) |
| C07D 487/04 | (2006.01) |
| A61P 31/16 | (2006.01) |
| A61K 31/506 | (2006.01) |
| A61K 31/53 | (2006.01) |
| A61K 45/06 | (2006.01) |
| C07D 403/12 | (2006.01) |
| C07D 417/14 | (2006.01) |

(52) U.S. Cl.
CPC .......... *C07D 403/04* (2013.01); *A61K 31/506* (2013.01); *A61K 31/53* (2013.01); *A61K 45/06* (2013.01); *A61P 31/16* (2018.01); *C07D 403/12* (2013.01); *C07D 417/14* (2013.01); *C07D 487/04* (2013.01)

(58) Field of Classification Search
CPC .................................................... C07D 403/04
See application file for complete search history.

(56) References Cited

U.S. PATENT DOCUMENTS

| 8,937,080 B2 | 1/2015 | Raboisson et al. |
| 9,422,250 B2 | 8/2016 | McGowan et al. |
| 9,598,378 B2 | 3/2017 | McGowan et al. |
| 9,617,289 B2 | 4/2017 | Tahri et al. |
| 2019/0047989 A1 | 2/2019 | Jonkers et al. |

FOREIGN PATENT DOCUMENTS

| WO | 2007041130 A3 | 4/2007 |
| WO | 2010148197 A1 | 12/2010 |
| WO | 2012032065 A1 | 3/2012 |
| WO | 2012083117 A1 | 6/2012 |
| WO | 2012083122 A1 | 6/2012 |
| WO | 2013019828 A1 | 2/2013 |
| WO | 2013184985 A1 | 12/2013 |

OTHER PUBLICATIONS

Chawla, et al., "Challenges in Polymorphism of Pharmaceuticals", Current Research & Information on Pharmaceutical Sciences, vol. 5(1): pp. 9-12 ( Jan.-Mar. 2004).
Clark, et al, "Discovery of a Novel, First-in-Class, Orally Bioavailable Azaindole Inhibitor (VX-787) of Influenza PB2", Journal of Medicinal Chemistry, vol. 57 (15): pp. 6668-6678 (Jul. 14, 2014).
Narayanan, et al, "Developments in antivirals against influenza, smallpox and hemorrhagic fever viruses", Expert Opinion on Investigational Drugs, vol. 20(2); pp. 239-254 (Feb. 1, 2011).
Newman, et al., "Solid-State Analysis of the Active Pharmaceutical Ingredient in Drug Products", Drug Discovery Today, Oct. 19, 2003, pp. 898-905, vol. 8(19).
International Search Report and Written Opinion for received for PCT/EP2016/078778, dated Jan. 11, 2017.

*Primary Examiner* — Paul V Ward

(57) ABSTRACT

The current invention relates to a compound of formula (I) which can be used for the treatment of, or against viral influenza infections.

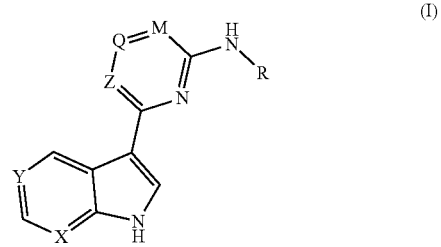

10 Claims, No Drawings

HETEROCYCLIC INDOLES FOR USE IN INFLUENZA VIRUS INFECTION

CROSS-REFERENCE TO RELATED APPLICATIONS

This application is a national phase entry of International Application No. PCT/EP2016/078778, filed on Nov. 25, 2016, which claims priority to EP Patent Application No. 15196811.2, filed Nov. 27, 2015, each of which are incorporated herein in their entirety.

Influenza is a serious public health problem with a high incidence in the human population resulting in regular large-scale morbidity and mortality. It is a highly contagious airborne disease that causes an acute febrile illness. Systemic symptoms vary in severity from mild fatigue to respiratory failure and death. According to the WHO the average global burden of annual epidemics may be on the order of 1 billion cases, 3-5 million cases of severe illness and 300,000-500,000 deaths annually. Every year, influenza viruses circulate in humans, typically affecting 5-20% of the population in all age groups, with this figure rising up to 30% during major epidemics. Rates of serious illness and death are highest among persons aged >65 years, children aged <2 years, and persons of any age who have medical conditions that place them at increased risk for complications from influenza, such as chronic heart, lung, kidney, liver, blood or metabolic diseases, or weakened immune systems. Although deaths are infrequent among children, rates of hospitalization range from approximately 100 to 500 per 100,000 for children <5 years-old, depending on the presence or absence of co-morbid conditions. Hospitalization rates among children aged <24 months are comparable to rates reported among persons aged >65 years.

In the US, annual influenza epidemics lead to approximately 30 million outpatient visits, resulting in medical costs of $10 billion annually. Lost earnings due to illness and loss of life represent a cost of over $15 billion annually and the total US economic burden of annual influenza epidemics amounts to over $85 billion.

Pathogens that cause influenza are negative sense, single-stranded RNA viruses, which belong to the family of Orthomyxoviridae. There are three types of influenza viruses: A, B and C. Influenza A viruses are the most common form, which can spread in mammals and birds. The subtypes of influenza A are named by the types of surface proteins hemagglutinin (H) and neuraminidase (N). There are 18 different hemagglutinin and 11 known neuraminidases. Current seasonal influenza viruses found in human are mainly H1N1 and H3N2 subtypes. Influenza B viruses are usually found only in humans. They are not divided into subtypes, but can be further broken down into different strains. Circulating influenza viruses are highly variable each year, and both influenza A and B cause seasonal epidemics all over the world. Influenza C viruses give much milder symptoms, which do not cause epidemics.

All three types of viruses have similar genome structures. The genome comprises 8 segments, encoding 9-11 proteins, depending on the type. Influenza A encodes 11 proteins, which includes the surface proteins (hemagglutinin (HA) and neuraminidase (NA), the polymerase complex (PA, PB1 and PB2), nucleoprotein (NP), membrane proteins (M1 and M2), and other proteins (NS1, NS2, NEP). Among the three influenza virus types, influenza A has the highest rate of mutation. Influenza B evolves slower than A, but faster than C. The segmented genome allows gene exchanging between different viral strains, which generate new variants of influenza viruses.

Influenza virus can be transmitted among humans by direct contact with infected individuals or virus-contaminated material. One can also be infected by inhalation of suspended virus droplets in the air. Those droplets are generated by coughing, sneezing or talking of infected individuals. Seasonal influenza is characterized by a sudden onset of high fever, cough (usually dry), headache, muscle and joint pain, severe malaise (feeling unwell), sore throat and runny nose. Cough can be severe and can last two or more weeks. Most people recover from fever and other symptoms within a week without requiring medical attention. But influenza can cause severe illness or death especially in people at high risk as mentioned above. The time from infection to illness, known as the incubation period, is about two days.

The most effective way to prevent the disease and/or severe outcomes from the illness is vaccination. Safe and effective vaccines are available and have been used for more than 60 years. Among healthy adults, influenza vaccines can provide reasonable protection. However, vaccination comes with several limitations. First, influenza vaccine may be less effective in preventing illness among the elderly, and may only reduce severity of disease and incidence of complications and deaths. In addition, influenza vaccination is most effective when circulating viruses are well-matched with vaccine viruses, and the success of vaccination is largely dependent on the good prediction of the most prevalent virus type of the season. Rapid and continual evolution of influenza viral strains through antigenic drift, coupled with the short-lived nature of vaccine-induced immune responses to current influenza vaccines, means that vaccination with seasonally appropriate strains is required every year for prevention.

The current treatment of influenza uses either direct antiviral drugs, or medicines that release the influenza-induced symptoms. There are two classes of influenza antiviral drugs available on the market: neuraminidase inhibitors and M2 channel inhibitors. Neuraminidase inhibitors, oseltamivir or zanamivir, are the primary antiviral agents recommended for the prevention and treatment of influenza. These are effective against both influenza type A and B viruses. Development of resistance to these antiviral drugs has been identified during treatment of seasonal influenza and in sporadic oseltamivir-resistant 2009 H1N1 virus, but the public health impact has been limited to date. M2 channel inhibitors, such as amantadine and rimantadine (amantadanes), are active against influenza A strains, but not influenza B strains. Amantadane resistance among circulating influenza A viruses increased rapidly worldwide beginning during 2003-2004.

Therefore, amantadine and rimantadine are not recommended for antiviral treatment or chemoprophylaxis of currently circulating influenza A virus strains.

In 2009, the novel swine H1N1 strain caused an unexpected influenza pandemic as a result of reassortment of genes from human, pig, and bird's H1N1 viruses. This past pandemic, together with the ongoing circulation of highly pathogenic avian H5N1 strains and the recent emergence of the H7N9 virus, a new reassortant of avian origin isolated in China, and associated with severe respiratory disease with 40% of mortality, which could potentially adapt for human-to-human transmission, highlighted the vulnerability of the world population to novel influenza strains. Although vaccination remains the main prophylactic strategy for controlling influenza infection, to bridge the period before a new vaccine becomes available and to treat the severe influenza cases, as well as to counter the problem of viral resistance, a wider choice of anti-influenza drugs is required. Development of new influenza antivirals has therefore again become a high priority and an unmet medical need.

The current invention relates to a compound of formula (I) which can be used for the treatment of, or against viral influenza infections:

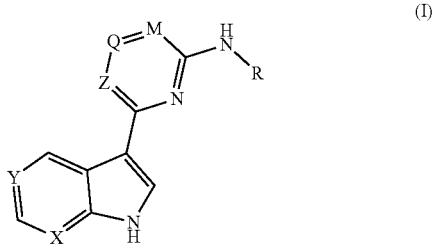

(I)

a stereo-isomeric form, a pharmaceutically acceptable salt, solvate or polymorph thereof, wherein X is N and Y is N; or X is C substituted by —F and Y is C substituted by —F, —Cl, —CH$_3$, or —CN;

Z is N, Q is selected from —C—CH$_3$, —C—COOH, —C—CF$_3$, —CH-cyclopropyl, —CH$_2$R$_1$, or —CONR$_1$R$_1$ and M is CF wherein R$_1$ is independently selected from hydrogen, halogen, cyano, oxo, alkyl, hydroxyl, amino; or Z is N, Q is N and M is CH; or Z is C, Q is N and M is CH; and R is C$_{3-8}$ cycloalkyl substituted by carboxylic acid, or —N—C(O)—C$_{3-6}$-heterocycle optionally substituted by C$_{1-6}$ alkyl or —COOH.

One of the most preferred compounds according to the current invention has the structural formula

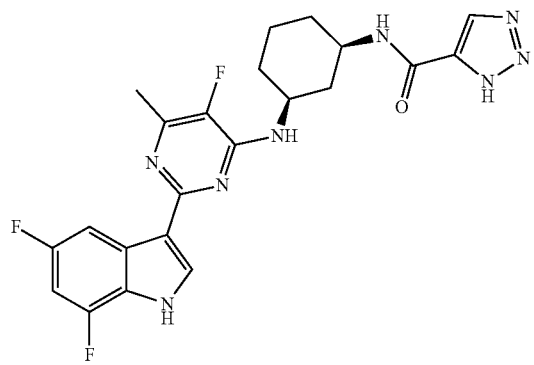 [SMILES: Cc1nc(-c2c[nH]c3c(F)cc(F)cc23)nc(N[C@H]2CCC[C@@H](NC(=O)c3cnn[nH]3)C2)c1F]

Part of the invention is also a pharmaceutical composition comprising a compound of formula (I) or a stereo-isomeric form, a pharmaceutically acceptable salt, solvate or polymorph thereof together with one or more pharmaceutically acceptable excipients, diluents or carriers.

The pharmaceutical composition may also include additional therapeutic agents, like another antiviral agent or an influenza vaccine, or both.

To the invention also belongs a compound of formula (I) or a stereo-isomeric form, a pharmaceutically acceptable salt, solvate or polymorph thereof, or a pharmaceutical composition for use as a medicament.

Additionally the invention relates to a compound of formula (I) or a stereo-isomeric form, a pharmaceutically acceptable salt, solvate or polymorph thereof or a pharmaceutical composition for use in the treatment of influenza.

Said use may also comprise the co-administration of an additional therapeutic agent, wherein said additional therapeutic agent is selected from an antiviral agent or influenza vaccine, or both.

The term "alkyl" refers to a straight-chain or branched-chain saturated aliphatic hydrocarbon containing the specified number of carbon atoms.

The term "cycloalkyl" refers to a carbo-cyclic ring containing the specified number of carbon atoms.

The term "heterocycle" refers to molecules that are saturated or partially saturated comprising one or more heteroatoms selected from N, O or S, in particular from N and O. Said heterocycle may have 4, 5, 6 or 7 ring atoms.

Pharmaceutically acceptable salts of the compounds of formula (I) include the acid addition and base salts thereof. Suitable acid addition salts are formed from acids which form non-toxic salts. Suitable base salts are formed from bases which form non-toxic salts.

The compounds of the invention may also exist in unsolvated and solvated forms. The term "solvate" is used herein to describe a molecular complex comprising the compound of the invention and one or more pharmaceutically acceptable solvent molecules, for example, ethanol.

The term "polymorph" refers to the ability of the compound of the invention to exist in more than one form or crystal structure.

The compounds of the present invention may be administered as crystalline or amorphous products. They may be obtained for example as solid plugs, powders, or films by methods such as precipitation, crystallization, freeze drying, spray drying, or evaporative drying. They may be administered alone or in combination with one or more other compounds of the invention or in combination with one or more other drugs. Generally, they will be administered as a formulation in association with one or more pharmaceutically acceptable excipients. The term "excipient" is used herein to describe any ingredient other than the compound(s) of the invention. The choice of excipient depends largely on factors such as the particular mode of administration, the effect of the excipient on solubility and stability, and the nature of the dosage form.

The compounds of the present invention or any subgroup thereof may be formulated into various pharmaceutical forms for administration purposes. As appropriate compositions there may be cited all compositions usually employed for systemically administering drugs. To prepare the pharmaceutical compositions of this invention, an effective amount of the particular compound, optionally in addition salt form, as the active ingredient is combined in intimate admixture with a pharmaceutically acceptable carrier, which carrier may take a wide variety of forms depending on the form of preparation desired for administration. These pharmaceutical compositions are desirably in unitary dosage form suitable, for example, for oral, rectal, or percutaneous administration. For example, in preparing the compositions in oral dosage form, any of the usual pharmaceutical media may be employed such as, for example, water, glycols, oils, alcohols and the like in the case of oral liquid preparations such as suspensions, syrups, elixirs, emulsions, and solutions; or solid carriers such as starches, sugars, kaolin, diluents, lubricants, binders, disintegrating agents and the like in the case of powders, pills, capsules, and tablets. Because of their ease in administration, tablets and capsules represent the most advantageous oral dosage unit forms, in which case solid pharmaceutical carriers are obviously employed. Also included are solid form preparations that can be converted, shortly before use, to liquid forms. In the compositions suitable for percutaneous administration, the carrier optionally comprises a penetration enhancing agent and/or a suitable wetting agent, optionally combined with suitable additives of any nature in minor proportions, which additives do not introduce a significant deleterious effect on the skin. Said additives may facilitate the administration to the skin and/or may be helpful for preparing the desired compositions. These compositions may be administered in various ways, e.g., as a transdermal patch, as a spot-on, as an ointment. The compounds of the present invention may also be administered via inhalation or insufflation by means of methods and formulations employed in the art for administration via this way. Thus, in general the compounds of the present invention may be administered to the lungs in the form of a solution, a suspension or a dry powder.

It is especially advantageous to formulate the aforementioned pharmaceutical compositions in unit dosage form for ease of administration and uniformity of dosage. Unit dosage form as used herein refers to physically discrete units suitable as unitary dosages, each unit containing a predetermined quantity of active ingredient calculated to produce the desired therapeutic effect in association with the required pharmaceutical carrier. Examples of such unit dosage forms are tablets (including scored or coated tablets), capsules, pills, powder packets, wafers, suppositories, injectable solutions or suspensions and the like, and segregated multiples thereof.

Those of skill in the treatment of infectious diseases will be able to determine the effective amount from the test results presented hereinafter. In general it iscontemplated that an effective daily amount would be from 0.01 mg/kg to 50 mg/kg body weight, more preferably from 0.1 mg/kg to 10 mg/kg body weight. It may be appropriate to administer the required dose as two, three, four or more sub-doses at appropriate intervals throughout the day. Said sub-doses may be formulated as unit dosage forms, for example, containing 1 to 1000 mg, and in particular 5 to 200 mg of active ingredient per unit dosage form.

The exact dosage and frequency of administration depends on the particular compound of formula (I) used, the particular condition being treated, the severity of the condition being treated, the age, weight and general physical condition of the particular patient as well as other medication the individual may be taking, as is well known to those skilled in the art.

Furthermore, it is evident that the effective amount may be lowered or increased depending on the response of the treated subject and/or depending on the evaluation of the physician prescribing the compounds of the instant invention. The effective amount ranges mentioned above are therefore only guidelines and are not intended to limit the scope or use of the invention to any extent.

The present disclosure is also intended to include any isotopes of atoms present in the compounds of the invention. For example, isotopes of hydrogen include tritium and deuterium and isotopes of carbon include C-13 and C-14.

The present compounds used in the current invention may also exist in their stereo-chemically isomeric form, defining all possible compounds made up of the same atoms bonded by the same sequence of bonds but having different three-dimensional structures, which are not interchangeable. Unless otherwise mentioned or indicated, the chemical designation of compounds encompasses the mixture of all possible stereo-chemically isomeric forms, which said compounds might possess.

Said mixture may contain all dia-stereomers and/or enantiomers of the basic molecular structure of said compound. All stereo-chemically isomeric forms of the compounds used in the present invention either in pure form or in admixture with each other are intended to be embraced within the scope of the present invention including any racemic mixtures or racemates.

Pure stereoisomeric forms of the compounds and intermediates as mentioned herein are defined as isomers substantially free of other enantiomeric or diastereomeric forms of the same basic molecular structure of said compounds or intermediates. In particular, the term 'stereoisomerically pure' concerns compounds or intermediates having a stereoisomeric excess of at least 80% (i. e. minimum 90% of one isomer and maximum 10% of the other possible isomers) up to a stereoisomeric excess of 100% (i.e. 100% of one isomer and none of the other), more in particular, compounds or intermediates having a stereoisomeric excess of 90% up to 100%, even more in particular having a stereoisomeric excess of 94% up to 100% and most in particular having a stereoisomeric excess of 97% up to 100%. The terms 'enantiomerically pure' and 'diastereomerically pure' should be understood in a similar way, but then having regard to the enantiomeric excess, respectively the diastereomeric excess of the mixture in question.

Pure stereoisomeric forms of compounds and intermediates used in this invention may be obtained by the application of art-known procedures. For instance, enantiomers may be separated from each other by the selective crystallization of their diastereomeric salts with optically active acids or bases. Examples thereof are tartaric acid, dibenzoyltartaric acid, ditoluoyltartaric acid and camphosulfonic acid. Alternatively, enantiomers may be separated by chromatographic techniques using chiral stationary phases. Said pure stereochemically isomeric forms may also be derived from the corresponding pure stereochemically isomeric forms of the appropriate starting materials, provided that the reaction occurs stereospecifically. Preferably, if a specific stereoisomer is desired, said compound will be synthesized by stereospecific methods of preparation. These methods will advantageously employ enantiomerically pure starting materials.

EXAMPLES

Scheme 1. Preparation of compound 6

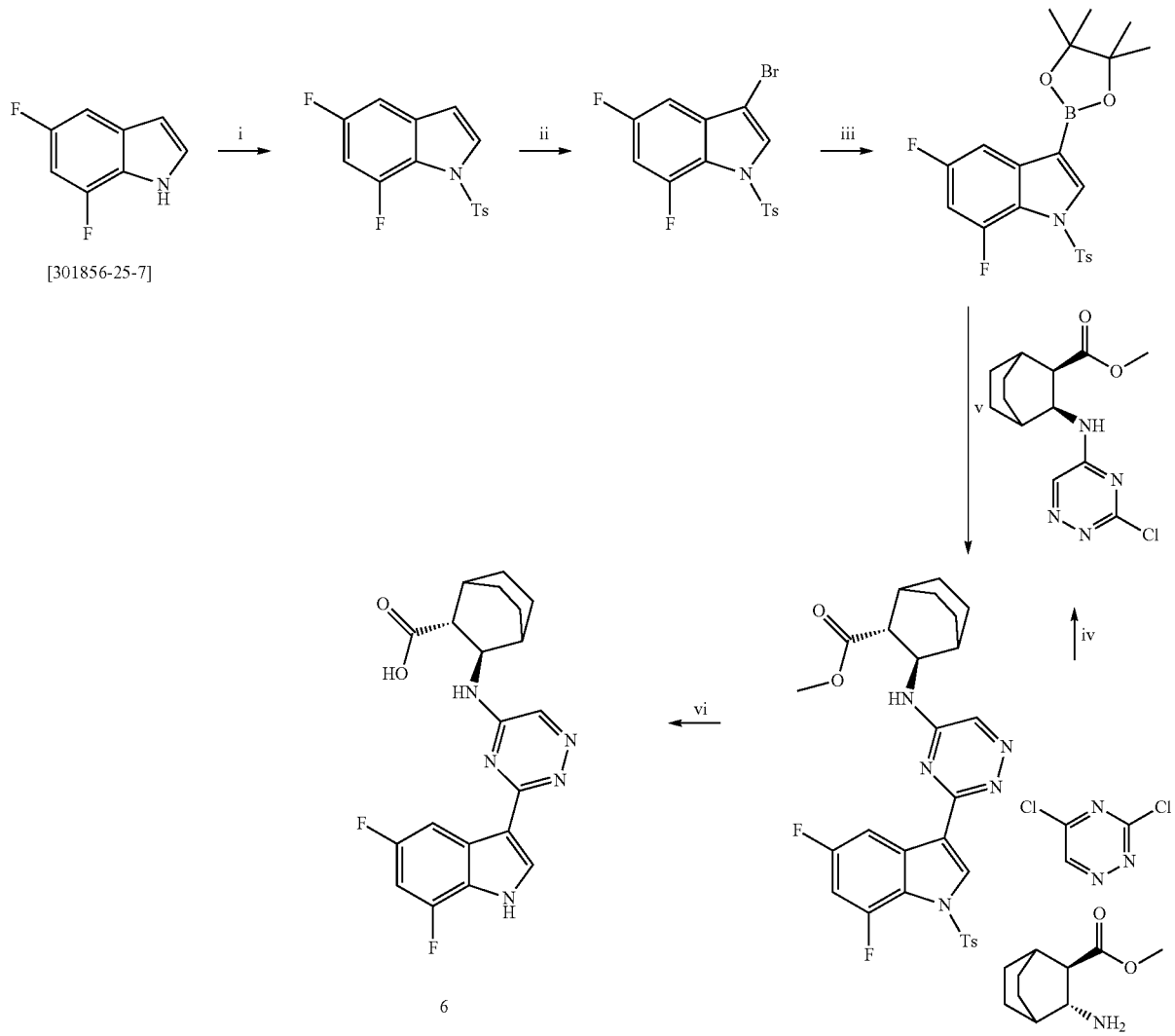

Scheme 1: i) TBAHS, NaOH, Toluene ii) NBS, DMF iii) 4,4,4',4',5,5,5',5'-Octamethyl-2,2'-bi-1,3,2-dioxaborolane, Pd(dppf)Cl$_2$, KOAc, 1,4-dioxane, 90° C. iv) DIPEA, 1,4-dioxane v) Na$_2$CO$_3$, Pd(PPh$_3$)$_4$, H$_2$O, 1,4-dioxane, 80° C. vi) LiOH, 1,4-dioxane Preparation of 1

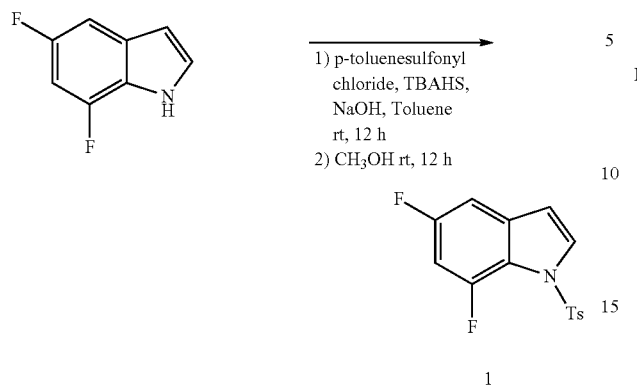

A solution of 5,7-difluoro-1H-indole (30 g, 195.91 mmol) in toluene (500 mL) was stirred under nitrogen. TBAHS (5 g, 14.7 mmol) was added, followed by NaOH (50% in H₂O) (105 mL), and the mixture was stirred vigorously. p-toluenesulfonyl chloride (63.5 g, 333.05 mmol) was added and the mixture was stirred overnight. The solution was diluted with 250 mL toluene and washed two times with water. The organic layer was dried over MgSO₄, the solids were removed by filtration, and the solvent of the filtrate was removed under reduced pressure. The crude was triturated in methanol and stirred overnight. The precipitate was collected by filtration and dried in vacuo, yielding 5,7-difluoro-1-tosyl-1H-indole, 1.

To a solution of 5,7-difluoro-1-tosyl-1H-indole, 1, (50.85 g, 165.46 mmol) in DMF (330 mL) was added NBS (35.34 g, 198.56 mmol) portion wise. Stirring was continued at 50° C. for one hour. The mixture was added drop wise to a stirred solution of NaOH (1N, 200 mL) in ice water (1 L) and stirred overnight. The precipitate was collected by filtration and dried in vacuo, yielding 3-bromo-5,7-difluoro-1-tosyl-1H-indole, 2.

Preparation of 3

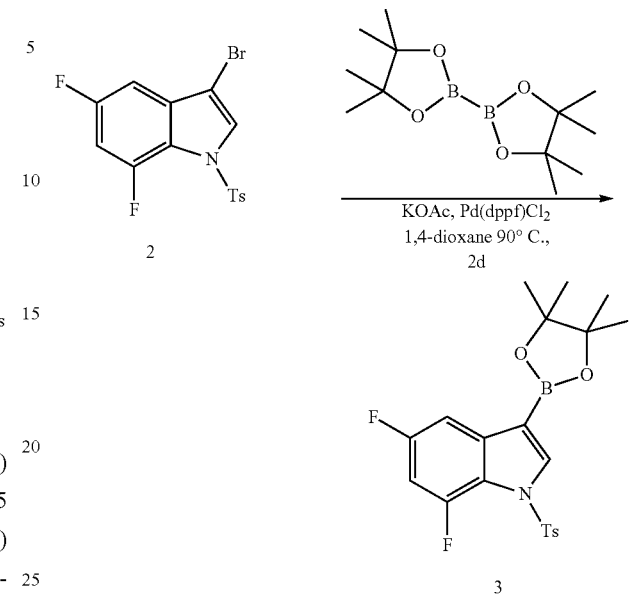

A mixture of 3-bromo-5,7-difluoro-1-tosyl-1H-indole, 2, (60 g, 155.35 mmol), 4,4,4',4',5,5,5',5'-octamethyl-2,2'-bi-1,3,2-dioxaborolane (118.35 g, 466.06 mmol), Pd(dppf)Cl₂ (22.74 g, 31.07 mmol) and KOAc (45.74 g, 466.06 mmol) in 1,4-dioxane (1500 mL) was heated to 90° C. overnight under N₂-atmosphere. The entire mixture was stirred for 18 hours at 90° C. After filtration and concentration, the crude was purified via silica gel chromatography using a CH₂Cl₂ to heptane gradient. The fractions containing pure product were pooled, and the solvents were removed under reduced pressure, yielding 5,7-difluoro-3-(4,4,5,5-tetramethyl-1,3,2-dioxaborolan-2-yl)-1-tosyl-1H-indole, 3.

Preparation of 4

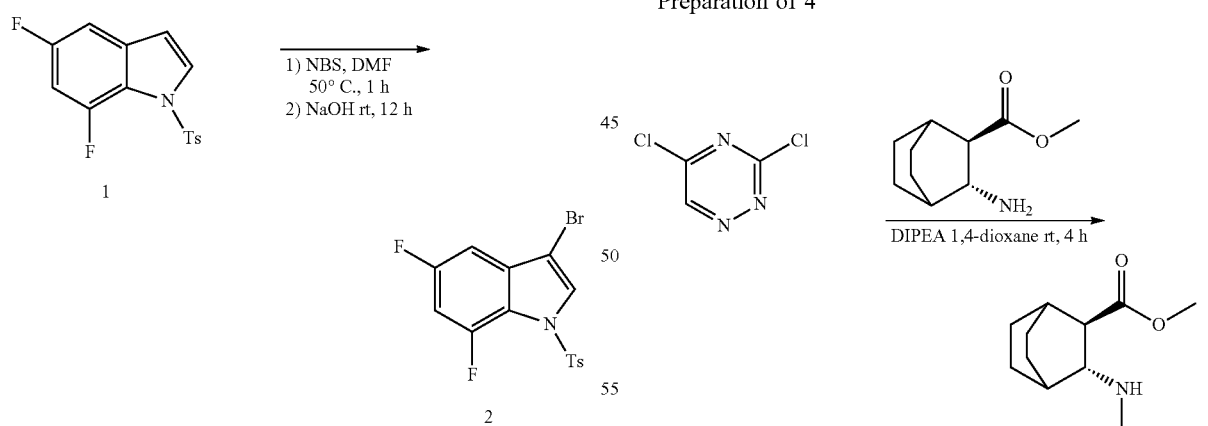

To a solution of 3,5-dichloro-1,2,4-triazine (250 mg, 1.67 mmol) in anhydrous 1,4-dioxane (35 mL) was added DIPEA (0.58 mL, 3.33 mmol) and (+/−)-(trans)-methyl 3-aminobicyclo-[2.2.2]octane-2-carboxylate (366 mg, 1.66 mmol).

The reaction mixture was stirred at room temperature for 4 hours. Ethyl acetate (100 mL) was added, and the organic solution was washed with aqueous saturated NH₄Cl solution, water, and brine. The organic layer was dried over MgSO₄, the solids were removed by filtration, and the solvent of the filtrate was removed under reduced pressure. The crude was purified by silica gel chromatography using an ethyl acetate to heptane gradient. The desired fractions were collected and the solvent was removed under reduced pressure, yielding (+/−)-(trans)-methyl 3-((3-chloro-1,2,4-triazin-5-yl)amino)bicyclo[2.2.2]octane-2-carboxylate, 4.

Preparation of 5

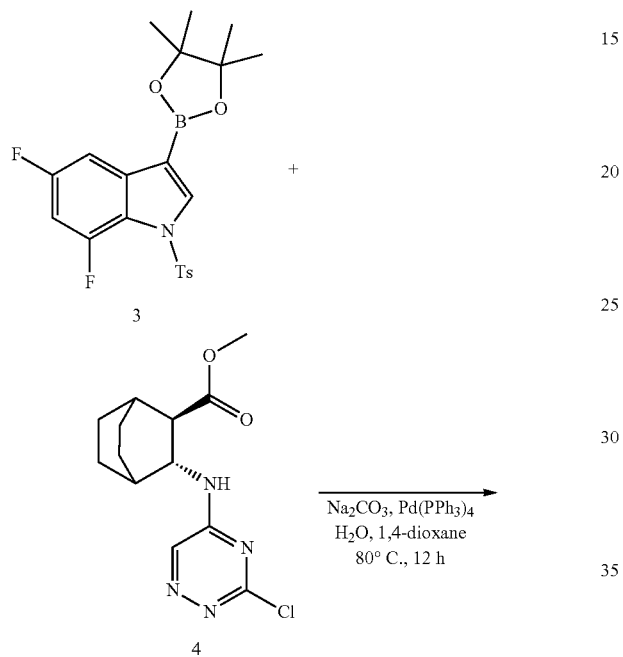

In a 250 mL round bottom flask, a mixture of 5,7-difluoro-3-(4,4,5,5-tetramethyl-1,3,2-dioxaborolan-2-yl)-1-tosyl-1H-indole, 3, (550 mg, 1.269 mmol), (+/−)-(trans)-methyl 3-((3-chloro-1,2,4-triazin-5-yl)amino)bicyclo[2.2.2]octane-2-carboxylate, 4, (313 mg, 1.06 mmol) and Na₂CO₃ (187 mg, 1.77 mmol) in H₂O (1 mL) and 1,4-dioxane (9 mL) was degassed with a stream of N₂ for 10 minutes. Pd(PPh₃)₄ (61 mg, 0.053 mmol) was added and the mixture was heated at 80° C. for 12 hours. The mixture was concentrated under reduced pressure and crude 5 was used without further purification in the next step.

Preparation of 6

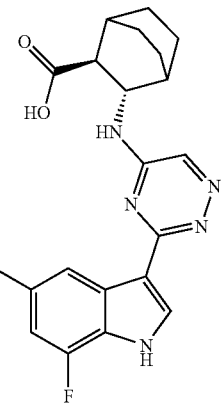

In a 100 mL flask 5 (300 mg, 0.53 mmol) was stirred in 1,4-dioxane (9 mL) at room temperature, while a solution of LiOH (13 mg, 0.53 mmol) in water, distilled (1 mL) was added. The mixture was heated between 80 and 90° C., and stirred for 4 hours. 1,4-dioxane was removed under reduced pressure and the crude was purified via preparatory HPLC (stationary phase: RP XBridge Prep C18 OBD-10 μm, 30×150 mm, mobile phase: 0.25% aq. NH₄HCO₃, CH₃CN). The desired fractions were collected and the solvent was removed under reduced pressure. The desired fractions were collected and the solvent was removed under reduced pressure, yielding 6. LC-MS ES⁺ m/z=400.1; Rt: 1.41 min, method D.

Scheme 2. Preparation of 13

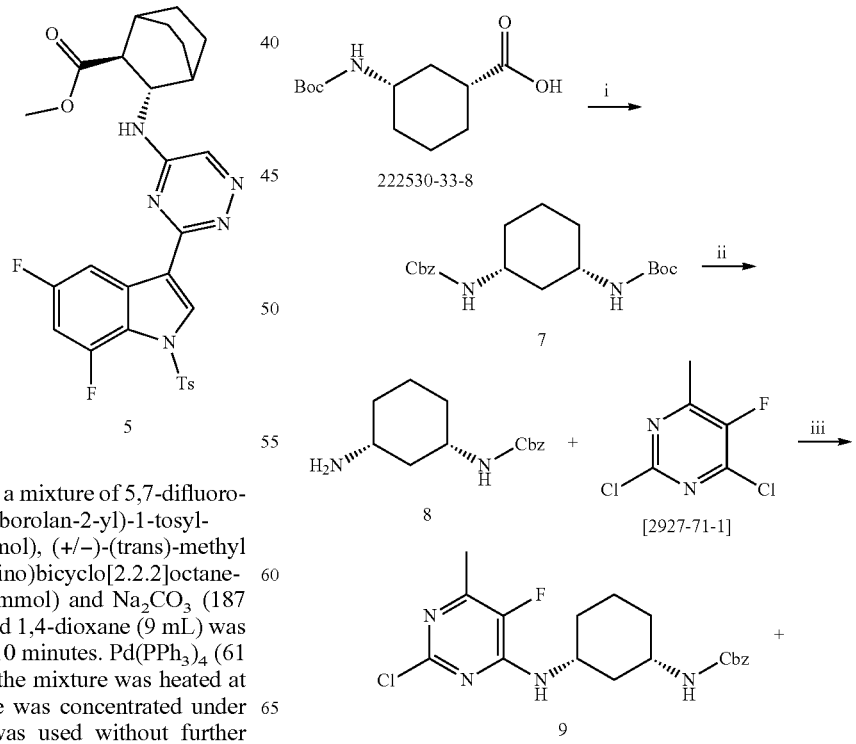

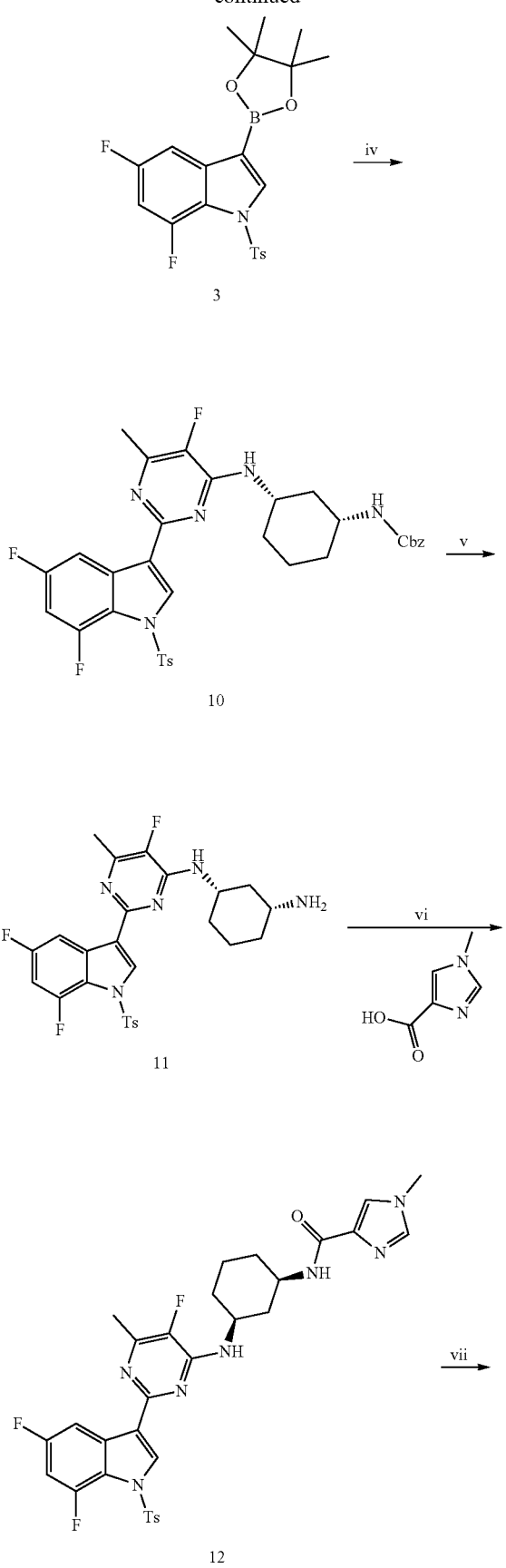

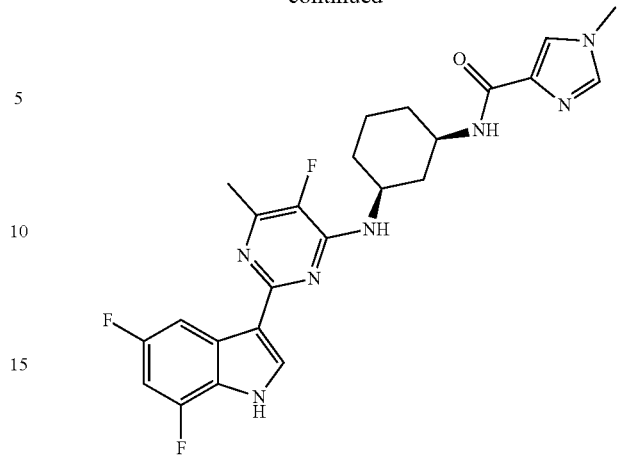

Scheme 2: i) DPPA, benzyl alcohol, Et₃N, toluene, 100° C., 12 h
ii) HCl, CH₂Cl₂, CH₃OH, rt, 48 h
iii) DIPEA, ACN, rt, 2 h
iv) Na₂CO₃, H₂O, 1,4-dioxane, 80° C., 24 h
v) TFA, rt, 50° C., 48 h
vi) DIPEA, HATU, ACN, DMF, rt, 24 h
vii) LiOH, H₂O, 1,4-dioxane, 60° C., 4 h Preparation of 7

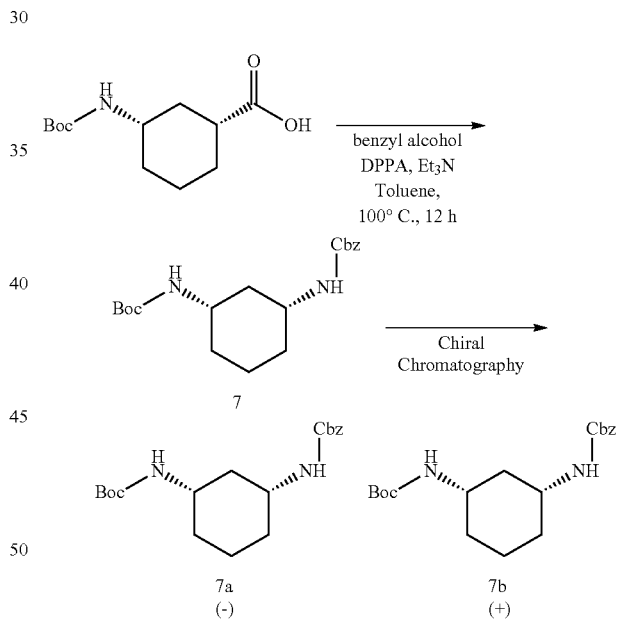

Et₃N (70 mL, 503 mmol) and DPPA (78 mL, 362 mmol) were added to a stirred solution of cis-3-[(tert-butoxycarbonyl)amino]cyclohexanecarboxylic acid (78 g, 321 mmol) in toluene (1 L), and the mixture was stirred at room temperature for 4 hours. Benzyl alcohol (66.4 mL, 641.2 mmol) was added, and the mixture was heated to 100° C. After 12 hours, the reaction mixture was cooled to room temperature, diluted with EtOAc. The organic layer was dried over MgSO₄, the solids were removed by filtration, and the solvent of the filtrate was removed under reduced pressure. The crude was purified via silica column chromatography using a heptane to ethyl acetate gradient. The fractions containing pure product were pooled, and the solvents were removed under reduced pressure to afford the racemic mixture. The chiral separation (stationary phase: Kromasil Amycoat 10 μm, mobile phase: gradient from 80% CO$_2$, 20% methanol to 80% CO$_2$, 20% methanol). The desired fractions were collected and the solvent was removed under reduced pressure to afford 7a, (−)-benzyl tert-butyl ((cis)-cyclohexane-1,3-diyl)dicarbamate, $[\alpha]_D^{20}$ −10.9 (c 0.47, DMF), and 7b, (+)-benzyl tert-butyl ((cis)-cyclohexane-1,3-diyl)dicarbamate, $[\alpha]_D^{20}$ +10.9 (c 0.52, DMF).

Preparation of 8

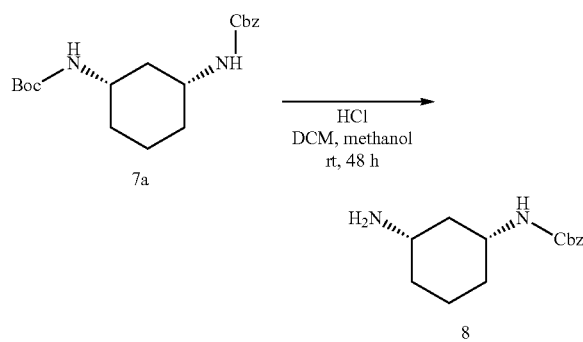

Into a 500 mL round bottom flask equipped with a magnetic stir bar, was added 7a (10 g, 28.7 mmol), CH$_2$Cl$_2$ (100 mL), and methanol (100 mL). 6M HCL in isopropanol was added slowly while stirring at room temperature and stirring continued for 48 hours. The solvent was removed under reduced pressure and the crude was stirred in diisopropylether containing isopropanol. The white precipitate was isolated by filtration and dried in vacuo yielding, 8. $^1$H NMR (360 MHz, DMSO-d$_6$) δ ppm 1.01-1.13 (m, 1H) 1.16-1.36 (m, 3H), 1.66-1.80 (m, 2H), 1.86-1.99 (m, 1H), 2.14 (m, 1H), 2.95-3.17 (m, 1H) 3.28-3.51 (m, 1H) 4.95-5.08 (m, 2H) 7.27-7.45 (m, 5H) 8.21 (s, 3H). LC-MS ES$^+$ m/z=249.3; Rt: 1.48 min, method B.

Preparation of 9

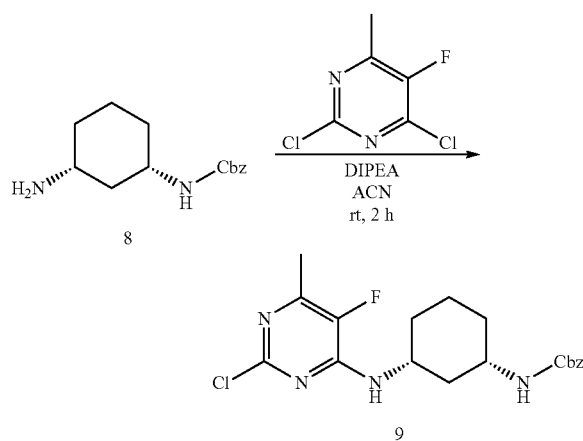

Into a 100 mL round bottom flask equipped with a magnetic stir bar was placed 2,4 dichloro-5-fluoro-6-methylpyrimidine (1 g, 5.53 mmol), ACN (35 mL), DIPEA (2.86 mL, 16.58 mmol), and 8 (1.6 g, 5.53 mmol). The reaction mixture was allowed to stir for 2 days at room temperature. The solvent was removed under reduced pressure. The crude was purified via silica column chromatography using a n-heptane to ethyl acetate gradient. The solvents of the best fractions were removed under reduced pressure to afford 9. $^1$H NMR (400 MHz, DMSO-d$_6$) δ ppm 1.08 (m, 2.5 Hz, 1H) 1.18-1.39 (m, 3H) 1.68-1.83 (m, 3H) 1.93-2.07 (m, 1H) 2.21 (m, 3H) 3.35-3.44 (m, 1H) 3.82-3.93 (m, 1H) 5.01 (s, 2H) 7.28-7.39 (m, 6H) 7.85 (m, 1H). LC-MS ES$^+$ m/z=393.2; Rt: 2.03 min, method B.

Preparation of 10

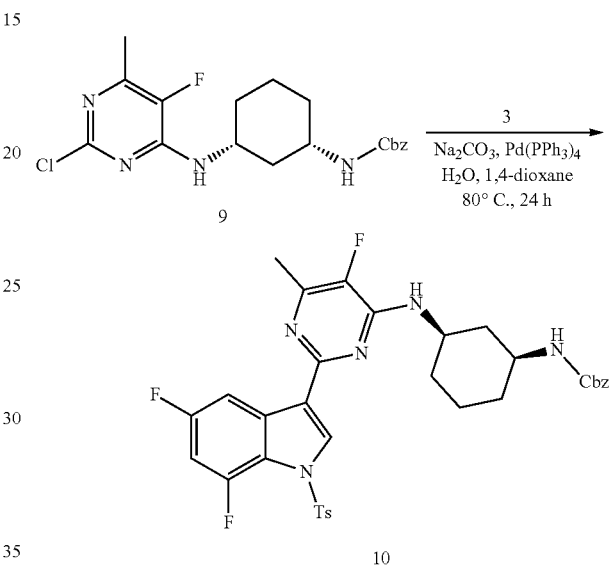

Into a 50 mL round bottom flask equipped with a magnetic stir bar was placed a mixture of 3 (500 mg, 1.15 mmol), 9 (378 mg, 0.96 mmol), sodium carbonate (210 mg, 1.98 mmol), water (1 mL) and 1,4-dioxane (10 mL). The yellow suspension was degassed with a stream of N$_2$ for 10 minutes. Pd(PPh$_3$)$_4$ (57 mg, 0.05 mmol) was added and the mixture was heated at 80° C. for 24 hours. The solids were removed by filtration and the solvent of the filtrate was removed under reduced pressure. The crude was purified via silica gel column chromatography using a n-hepane to ethyl acetate gradient. The solvents of the best fractions were removed under reduced pressure to afford 10. LC-MS ES$^+$ m/z=664.5; Rt: 2.65 min, method B.

Preparation of 11

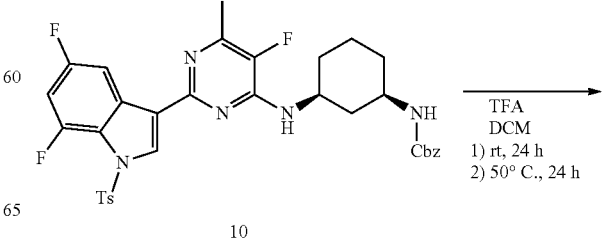

-continued

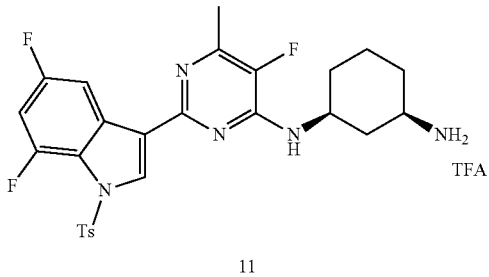

11

Into a 50 mL round bottom flask equipped with a magnetic stir bar was placed 10 (270 mg, 0.407 mmol), CH$_2$Cl$_2$ (5 mL), and TFA (10 mL). The reaction mixture was allowed to stir at room temperature for 24 hours. Additional TFA (10 mL) was added and the mixture was heated to 50° C. for 24 hours. The solvent was removed under reduced pressure to afford crude 11, which is used in the next step without further purification. LC-MS ES$^+$ m/z=530.2; Rt: 1.13 min, method A.

Preparation of 12

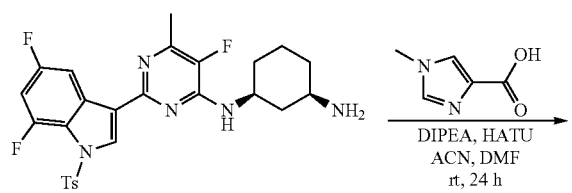

Into a 50 mL round bottom flask equipped with a magnetic stir bar was placed 1-methyl-1H-imidazole-4-carboxylic acid (121 mg, 0.93 mmol), DMF (10 mL), ACN (20 mL), DIPEA (0.321 mL, 1.864 mmol), and HATU (378 mg, 0.99 mmol). This mixture was allowed to stir 5 min at room temperature, afterwards 11 (400 mg, 0.621 mmol) was added. The flask was sealed and allowed to stir at room temperature for 24 hours. The reaction mixture was reduced in volume, then poured into water (400 mL), and partitioned with ethyl acetate (3×100 mL). The organic layers were combined, dried over sodium sulfate, the solids were removed by filtration, and the solvent of the filtrate was removed under reduced pressure. The crude was purified by silica gel column chromatography using a n-heptane to ethyl acetate gradient. The best fractions were pooled and the solvent was removed under reduced pressure to afford 12. LC-MS ES$^+$ m/z=638.5; Rt: 2.34 min, method B.

Preparation of 13

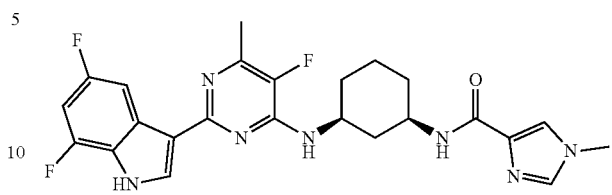

In a 100 mL flask 12 (230 mg, 0.361 mmol) was stirred in 1,4-dioxane (9 mL) at 60° C., while a solution of LiOH (86 mg, 3.61 mmol) in water (1 mL) was added. The mixture was brought to reflux for 1 hour and was allowed to stir overnight at ambient temperature. 1,4-dioxane was evaporated and the crude was reconstituted in ethyl acetate (20 mL), stirred and neutralized with conc. HCl. The solvent was removed under reduced pressure. The crude was purified via preparatory HPLC (stationary phase: RP XBridge Prep C18 ODB 5 μm, 30×250 mm, mobile phase: 0.25% NH$_4$HCO$_3$ solution in water, CH$_3$OH). The desired fractions were collected and evaporated to dryness. After addition of CH$_3$OH the solution was concentrated a second time to afford 13. $^1$H NMR (360 MHz, DMSO-d$_6$) δ ppm 1.26-1.57 (m, 4H) 1.84 (m, 2H) 2.07 (m, 2H) 2.32 (d, J=2.6 Hz, 3H) 3.67 (s, 3H) 3.92 (m, 1H) 4.08-4.20 (m, 1H) 7.05 (m, 1H) 7.35 (d, J=7.3 Hz, 1H) 7.60-7.67 (m, 2H) 7.72 (d, J=8.4 Hz, 1H) 8.05 (m, 1H) 8.11 (d, J=2.2 Hz, 1H) 12.17 (s, 1H). LC-MS ES$^+$ m/z=484.2; Rt: 1.87 min, method B. $[α]_D^{20}$ −137.6° (c 0.8, DMF)

Preparation of 14

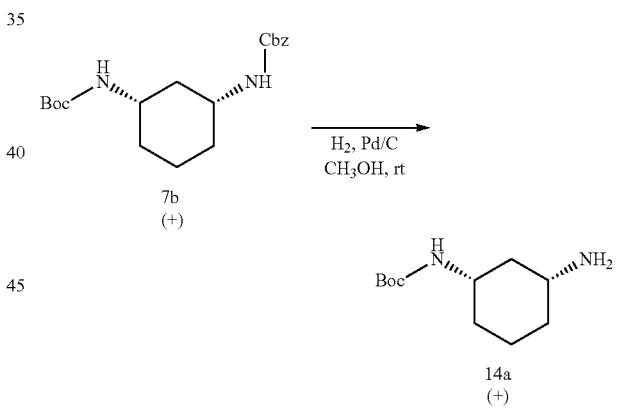

Step 1. (+)-7b (7 g, 20.09 mmol) was dissolved in CH$_3$OH, then Pd/C (855 mg) was added under inert atmosphere. The atmosphere of the reactor was remove and then replaced with hydrogen. The mixture was stirred under H$_2$ (10 bar) at 25° C. for 18 h. The H$_2$ was removed, then the mixture was filtered through Celite, and the solvent was removed under reduced pressure to afford an oil. LC-MS ES$^+$ m/z=215.1; Rt: 0.727 min, method F.

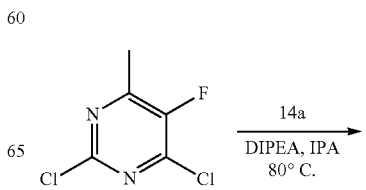

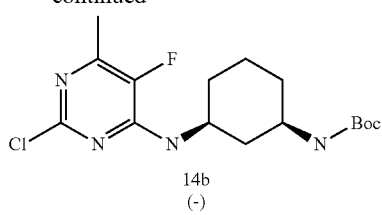

14b
(-)

Step 2. To a solution of 14a (3.08 g, 14.36 mmol) in isopropanol (150 mL) was added DIPEA (3.33 mL, 19.15 mmol) and then 2,4-dichloro-5-fluoro-6-methyl-pyrimidine (2.89 g, 15.96 mmol). The mixture was heated to 80° C. for 3 h. The solvent was removed under reduced pressure and the crude was reconstituted in $CH_2Cl_2$. The organic layer was washed with water, dried over $MgSO_4$, the solids were removed by filtration, and the solvent of the filtrate was removed under reduced pressure. The crude was purified via silica gel chromatography using a n-heptane to ethyl acetate gradient. The fractions containing pure product were pooled, the solvent was removed under reduced pressure to afford 14b. LC-MS ES$^+$ m/z=359.1; Rt: 0.963, method: E. $[\alpha]_D^{23}$–72.5° (c 0.14, $CH_3OH$)

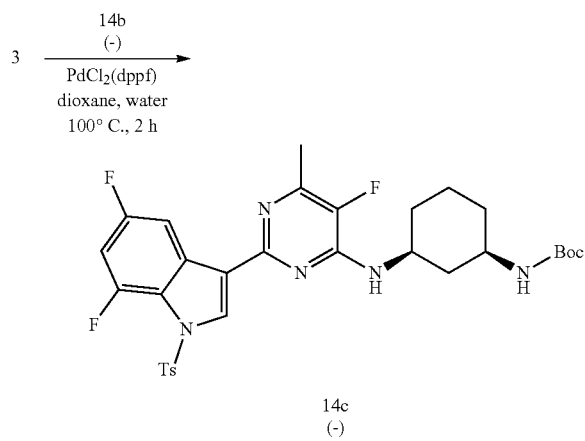

14c
(-)

Step 3. A mixture of 3 (2.8 g, 6.46 mmol), 14b (2.32 g, 6.46 mmol), $PdCl_2(dppf)$ (421 mg, 0.65 mmol) and $K_3PO_4$ (4.12 g, 19.39 mmol) in 1,4-dioxane (10 mL, degassed with $N_2$) and water (1 mL) was heated to 100° C. for 2 hours. The reaction mixture was filtered over celite and the solvent of the filtrate was reduced in volume under reduced pressure. The crude was partitioned between water and $CH_2Cl_2$. The organic layer was dried over $MgSO_4$, the solids were removed by filtration and the solvent of the filtrate was evaporated to dryness. The crude was purified via silica gel column chromatography using a heptane to ethyl acetate gradient. The fractions containing pure product were pooled, the solvent was removed under reduced pressure to afford 14c. LC-MS ES$^+$ m/z=630.2; Rt: 1.45, method: E. $[\alpha]_D^{23}$–57.6° (c 0.13, $CH_3OH$).

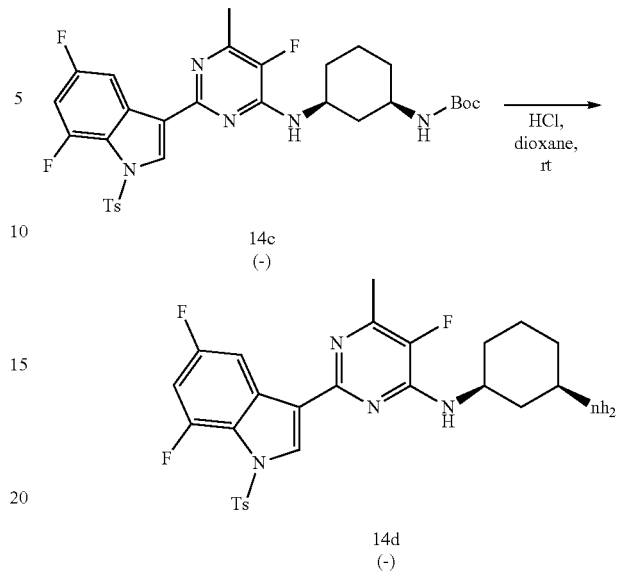

14c
(-)

14d
(-)

Step 4. 14c (3.25 g, 5.16 mmol) was dissolved in 1,4-dioxane (50 mL), and then 4M HCl in dioxane (7.74 mL) was added slowly. Then, conc. HCl (1.5 mL) was added. The solution was stirred at room temperature for 1 hour. Then, the reaction was quenched by addition of $NaHCO_3$ (sat., aq., 5 mL). The suspension was washed with $CH_2Cl_2$. The organic layer was evaporated to dryness to afford 14d that was used without further purification. LC-MS ES$^+$ m/z=530.2; Rt: 0.982, method: E.

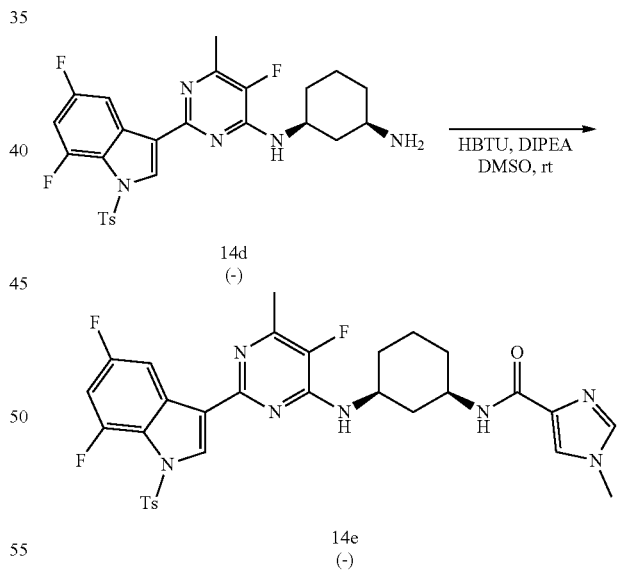

14d
(-)

14e
(-)

Step 5. To a flask containing 1-methyl-1H-pyrazole-4-carboxylic acid (188 mg, 1.49 mmol) in THF (14 mL) was added HBTU (1.074 g, 2.83 mmol) at room temperature for 5 minutes, under inert atmosphere then a solution of 14d and DIPEA (0.62 mL, 3.54 mmol) in DMSO was added. The mixture was stirred at room temperature for 1 h. Then was diluted with water and extracted with ethyl acetate. The organic layers were concentrated under reduced pressure to afford 14e that was used without further purification. LC-MS ES$^+$ m/z=638.2; Rt: 1.21, method: E.

Preparation of 17

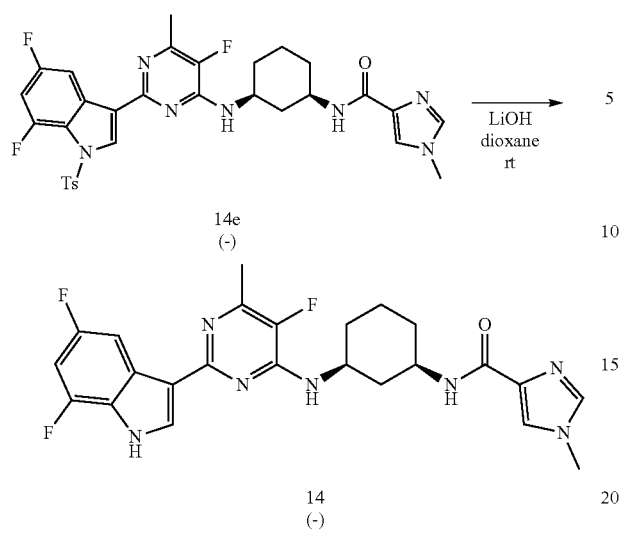

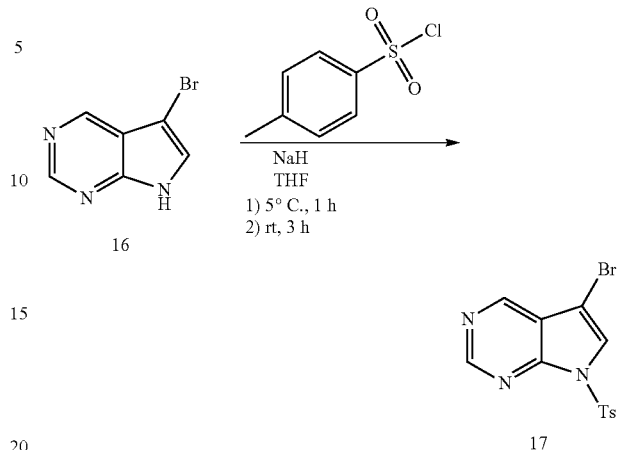

Step 6. Into a 100 mL flask was placed (−)-14e (230 mg, 0.36 mmol) in 1,4-dioxane (9 mL) at 60° C., while a solution of LiOH (86 mg, 3.6 mmol) in water (1 mL) was added and the mixture was stirred at room temperature overnight under inert atmosphere. Then, the solvent was removed under vacuum and the residue was partitioned between water and ethyl acetate. The organic layer was evaporated to dryness. The crude was purified via silica gel chromatography using isocratic ethyl acetate to afford (−)-14. LC-MS ES⁺ m/z=438.9; Rt: 2.28, method: C. $[\alpha]_D^{23}$ −202.3° (c 0.14, CH$_3$OH). MP>300° C.

Preparation of 16

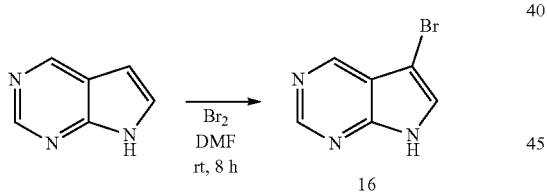

To a stirred solution of 7H-pyrrolo[2,3-d]pyrimidine (11.5 g, 73.92 mmol) in DMF (350 mL) was added a solution of bromine (11.8 g, 73.84 mmol) in DMF (50 mL) at 0° C. The cooling bath was removed and the reaction stirred at 20° C. for 8h, then the reaction mixture was poured into ice-water and basified with Na$_2$CO$_3$. The mixture was extracted with ethyl acetate. The combined organic layers were washed with 10% aq. Na$_2$S$_2$O$_3$ solution, brine, dried over MgSO$_4$, the solids were removed by filtration, and the filtrate was concentrated under reduced pressure to afford 16, 5-bromo-7H-pyrrolo-[2,3-d]pyrimidine as yellow solid, used in the next step without further purification. ¹H NMR (400 MHz, DMSO-d$_6$) δ ppm 7.84 (s, 1H), 8.84 (s, 1H), 8.92 (s, 1H), 12.57 (br, 1H).

To a stirred solution of 5-bromo-7H-pyrrolo[2,3-d]pyrimidine (12.8 g, 55.11 mmol) in THF was added NaH (4.48 g, 112.01 mmol) portion wise at 0° C. under nitrogen. The mixture was stirred at 5° C. for 1 hour then p-toluenesulfonyl chloride (11.6 g, 60.85 mmol) was added portion wise. The reaction mixture was allowed to warm to 20° C. and stirred for 3 hours. The reaction mixture was poured into a mixture of ice and 1M aq. HCl while stirring. The mixture was extracted with ethyl acetate. The combined organic layers were washed with brine, dried over MgSO$_4$, the solids were removed by filtration and the filtrate was concentrated under reduced pressure. The crude was purified by crystallization from ethyl acetate to afford 17, 5-bromo-7-tosyl-7H-pyrrolo[2,3-d]pyrimidine as white solid. ¹H NMR (400 MHz, DMSO-d$_6$) δ ppm 2.36 (s, 3H), 7.47 (d, J=8.0 Hz, 2H), 8.06 (d, J=8.0 Hz, 2H), 8.31 (s, 1H), 9.03 (s, 1H), 9.06 (s, 1H). LC-MS ES⁺ m/z=351.8; Rt: 2.02 min, method D.

Preparation of 18

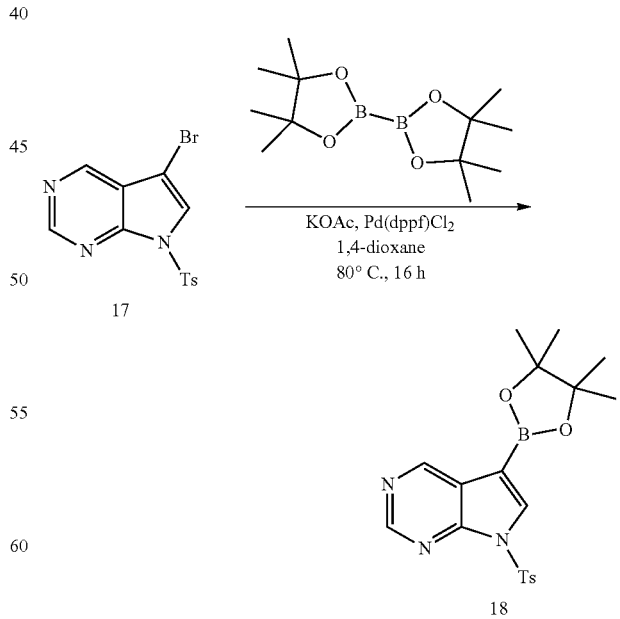

A mixture of 5-bromo-7-tosyl-7H-pyrrolo[2,3-d]pyrimidine (10 g, 28.39 mmol), bis(pinacolato)diboron (14.42 g, 56.79 mmol), potassium acetate (8.36 g, 85.18 mmol), Pd(dppf)Cl$_2$ (1 g, 1.37 mmol) in 1,4-dioxane (170 mL, degassed with nitrogen) was heated at 80° C. for 16 hours under nitrogen in a 500 mL round bottom flask equipped with a reflux condenser. The reaction mixture was cooled to room temperature, filtered through packed Celite and the solid was rinsed with ethyl acetate. The filtrate was concentrated under reduced pressure and the crude was purified by silica column chromatography using a n-heptane to ethyl acetate gradient. The desired fractions were collected and concentrated under reduced pressure to afford 18, 5-(4, 4, 5, 5-tetramethyl-1,3,2-dioxaborolan-2-yl)-7-tosyl-7H-pyrrolo [2,3-d]pyrimidine. $^1$H NMR (400 MHz, DMSO-d$_6$) δ ppm 1.33 (s, 12H) 2.37 (s, 3H) 7.47 (d, J=8.36 Hz, 2H) 8.11 (d, J=8.58 Hz, 2H) 8.14 (s, 1H) 9.00 (s, 1H) 9.10 (s, 1H). LC-MS ES$^+$ m/z=318.1; Rt: 0.74 min, method A.

Preparation of 19

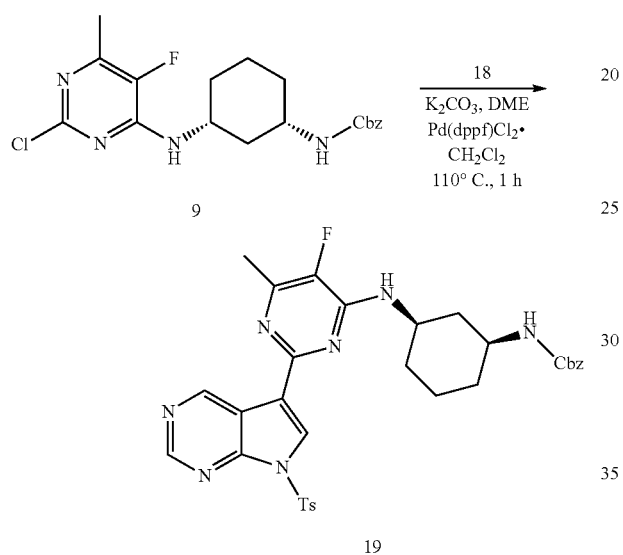

In a sealed tube, a solution of 18 (1.525 g, 3.82 mmol), 9 (1.6 g, 4.073 mmol), and K$_2$CO$_3$ (5.73 mL, 2 M, 11.46 mmol) in DME (24 mL) was purged with N$_2$ for 5 min and then Pd(dppf)Cl$_2$.CH$_2$Cl$_2$ (313 mg, 0.38 mmol) was added. The mixture was stirred and heated in an autoclave at 110° C. for 60 min, then was filtered over dicalite and the filtrate was concentrated under reduced pressure. The crude was purified via silica column chromatography using a n-heptane to 25% EtOAc in n-heptane gradient. The solvents of the best fractions were removed under reduced pressure to afford a solid. LC-MS ES$^+$ m/z=630.2; Rt: 1.28 min, method A.

Preparation of 20

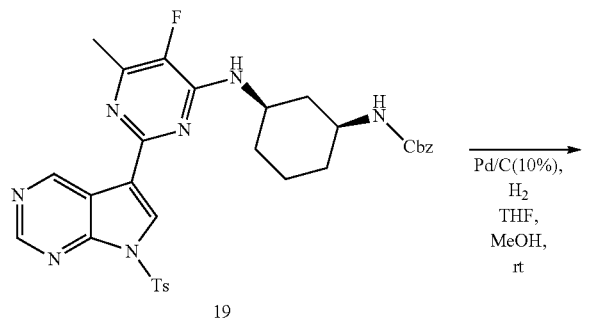

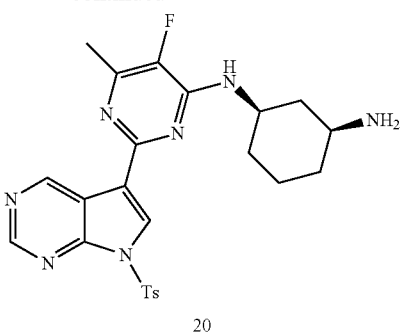

Pd/C (10%) (173 mg, 0.163 mmol) was added to a mixture of CH$_3$OH (15 mL) and THF (15 mL) under N$_2$ atmosphere. Afterwards, 19 (410 mg, 0.651 mmol) was added and the reaction mixture was stirred at a temperature of 25° C. under H$_2$ atmosphere until 1 eq. hydrogen was consumed. The catalyst was removed by filtration over Dicalite. The filtrate was concentrated under reduced pressure. The residue was dissolved in CH$_2$Cl$_2$ and treated with 6N HCl in isopropanol. The precipitate was dried in vacuo to afford 20.

Preparation of 21

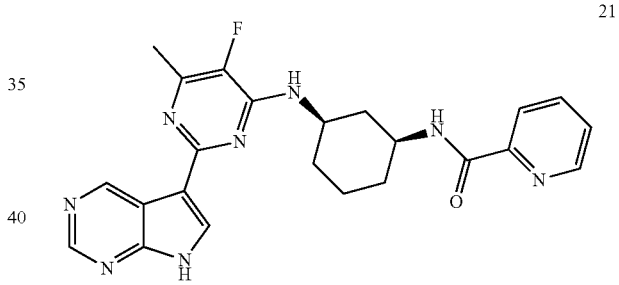

To a flask containing HBTU (478 mg, 1.26 mmol) in THF (3 mL) was added picolinic acid (93 mg, 0.76 mmol) at room temperature. The mixture was stirred for 5 minutes under inert atmosphere. Then a solution of 20 (250 mg, 0.504 mmol) and N,N-diisopropyl-ethylamine (0.22 mL, 1.261 mmol) in DMSO (1 mL) was added. The mixture was stirred at room temperature for 1h. Then, the reaction mixture was diluted with water and extracted with CH$_2$Cl$_2$. The organic layers were dried (MgSO$_4$), the solids were removed by filtration, and the filtrate concentrated under reduced pressure. The crude was purified by preparatory HPLC (RP SunFire Prep C18 OBD-10 μm, 30×150 mm, mobile phase 0.25% aq. ammonium carbonate, to acetonitrile). The best fractions were pooled and the solvents were removed under reduced pressure, yielding 21. MP:225.1 LC-MS ES$^+$ m/z=447.1; Rt: 2.18 min, method C. $[\alpha]_D^{23}$ −175.6° (c 0.13, CH$_3$OH). $^1$H NMR (300 MHz, METHANOL-d$_4$) δ ppm 1.28-1.59 (m, 3H) 1.61-1.75 (m, 1H) 1.94-2.25 (m, 3H) 2.38 (d, J=2.9 Hz, 3H) 2.39-2.47 (m, 1H) 4.08-4.20 (m, 1H) 4.26-4.37 (m, 1H) 7.53 (m, 1H) 7.94 (t, J=7.5 Hz, 1H) 8.08 (d, J=7.8 Hz, 1H) 8.20 (s, 1H) 8.61 (m, 1H) 8.79 (s, 1H) 9.73 (s, 1H)

Preparation of 22

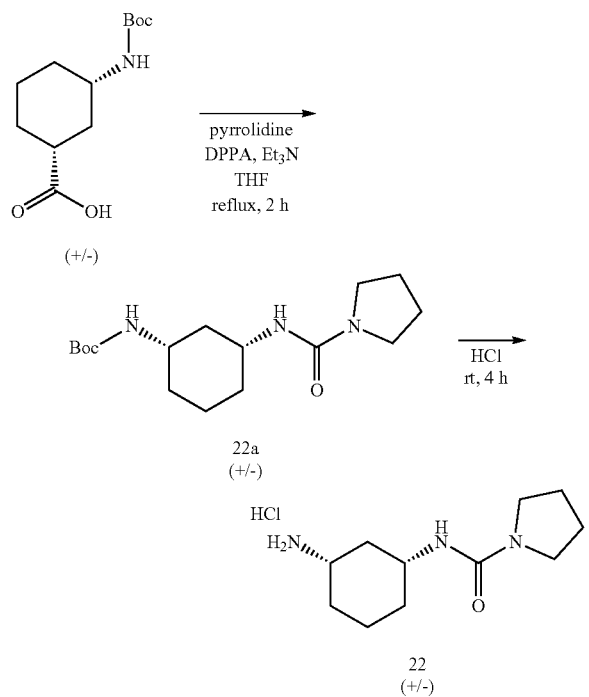

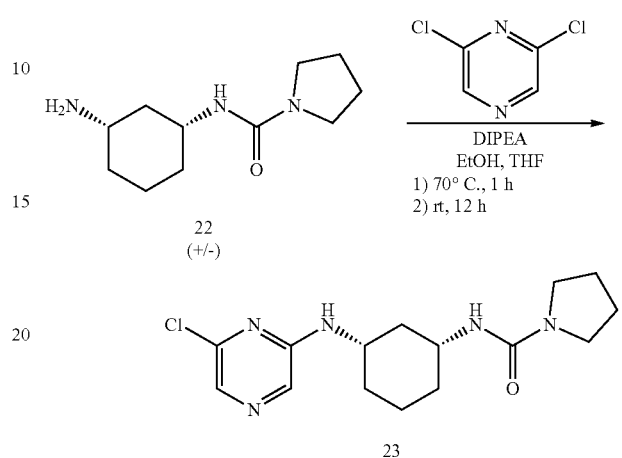

A mixture of (+/−)-cis-3-(boc-amino)cyclohexanecarboxylic acid (9.51 g, 39.09 mmol), diphenyl phosphoryl azide (12.61 mL, 58.63 mmol) and Et$_3$N (7.61 mL, 54.72 mmol) in THF (250 mL) was refluxed for 2 hours. The solution was allowed to reach room temperature, then pyrrolidine (9.81 mL, 117.26 mmol) was added and the solution was refluxed for 1 hour. The mixture was cooled to 0° C., the precipitate was isolated by filtration and washed with THF, dried in vacuo to afford 22a, t-butyl (+/−)-(cis-3-(pyrrolidine-1-carboxamido)cyclohexyl)carbamate, as a white powder.

A solution of (+/−)-t-butyl (cis-3-(pyrrolidine-1-carboxamido)cyclohexyl)carbamate (23.77 g, 76.33 mmol) in HCl (4 M in 1,4-dioxane, 344 mL) was stirred at room temperature for 4 hours. The solution was concentrated under reduced pressure and then dried in vacuo to afford 22, (+/−)-N-((cis)-3-aminocyclohexyl)pyrrolidine-1-carboxamide HCl as a white solid, that was used in the next step without further purification.

Preparation of 23

A solution of 2,6-dichloropyrazine (2.76 g, 18.65 mmol) was stirred at room temperature in ethanol (70 mL) and THF (70 mL). (+/−)-cis-N-(3-aminocyclohexyl) pyrrolidine-1-carboxamide (4.1 g, 19.41 mmol) and DIPEA (8.56 mL, 49 mmol) was added drop wise to the reaction mixture and stirred for one hour at 70° C. and then overnight at ambient temperature. The solvent was removed under reduced pressure, reconstituted in water, and extracted twice with CH$_2$Cl$_2$. The combined organic layers were washed with water, dried over MgSO$_4$, the solids were removed by filtration, and the solvent of the filtrate was removed under reduced pressure. The crude was purified by silica gel column chromatography using a CH$_2$Cl$_2$ to CH$_2$Cl$_2$/methanol gradient. The desired fractions were pooled and evaporated to dryness to afford 23.

Preparation of 24

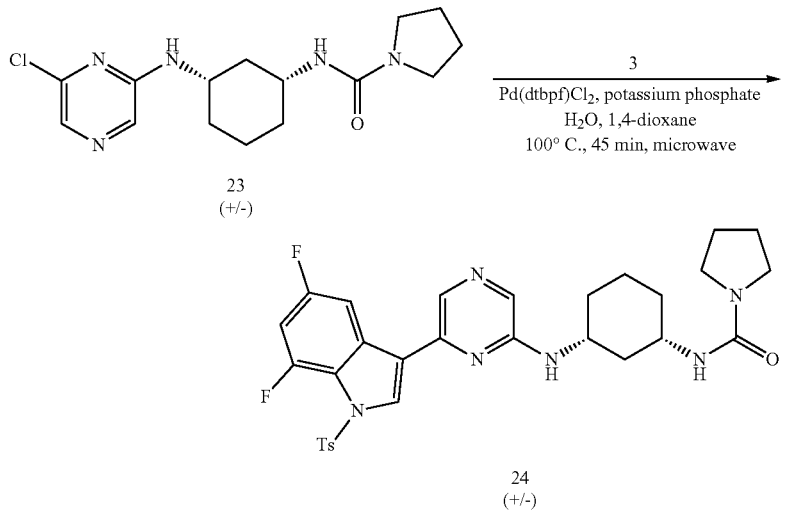

A mixture of 3 (350 mg, 0.81 mmol), 23 (157 mg, 0.485 mmol), 1,1'-bis(di-tert-butylphosphino)ferrocene palladium dichloride (53 mg, 0.08 mmol) and potassium phosphate tribasic (514 mg, 2.42 mmol) in 1,4-dioxane (10 mL) and H$_2$O (1 mL) was heated to 100° C. for 45 minutes under microwave irradiation. The reaction mixture was concentrated and the residual fraction was dissolved in CH$_2$Cl$_2$, and filtered. The filtrate was purified by silica gel column chromatography using a CH$_2$Cl$_2$ to CH$_2$Cl$_2$/methanol gradient. The desired fractions were collected and concentrated under reduced pressure, yielding 24. LC-MS ES$^+$ m/z=595.3; Rt: 2.09 min, method B.

Preparation of 25

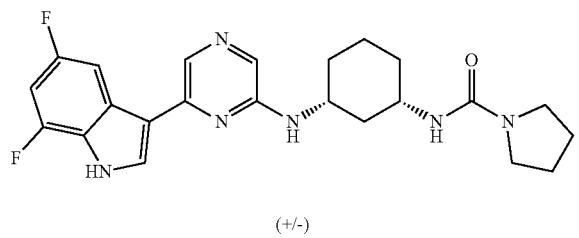

(+/-)

Compound 25 was prepared according to the methods to prepare 13. $^1$H NMR (400 MHz, DMSO-d$_6$) δ ppm 1.01-1.12 (m, 1H) 1.15-1.26 (m, 1H) 1.28-1.48 (m, 2H) 1.74-1.91 (m, 2H) 1.74-1.91 (m, 4H) 2.13 (m, 2H) 3.15-3.27 (m, 4H) 3.59 (m, 1H) 3.78-3.88 (m, 1H) 5.81 (m, 1H) 6.92 (m, 1H) 7.05 (m, 1H) 7.66 (s, 1H) 8.05 (m, 1H) 8.25 (s, 1H) 8.21-8.28 (m, 1H) 12.16 (s, 1H). LC-MS ES$^+$ m/z=441.4; Rt: 1.77 min, method B.

Preparation of 26

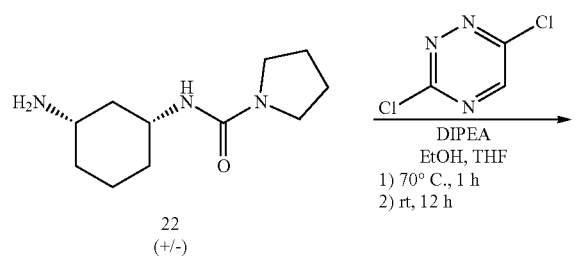

22
(+/-)

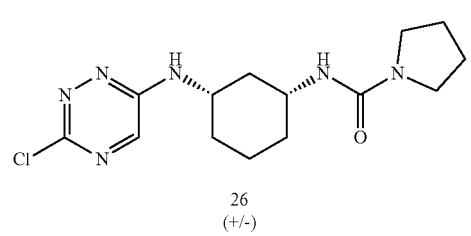

26
(+/-)

Intermediate 26 was prepared according to the methods to prepare 23.

Preparation of 27

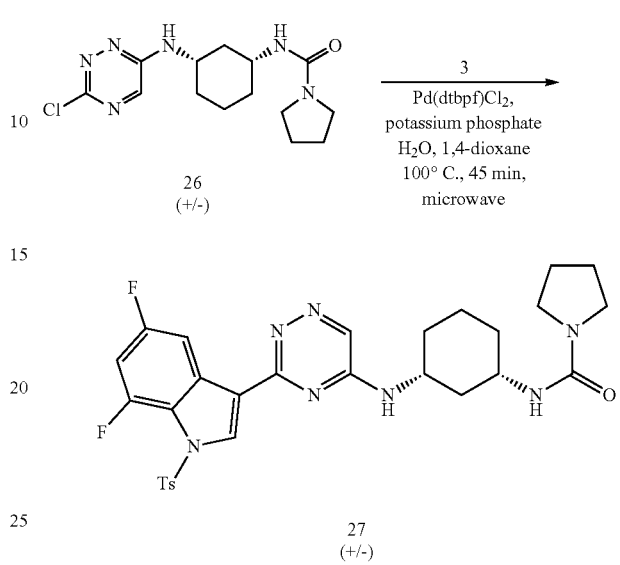

Intermediate 27 was prepared according to the methods to prepare 24. LC-MS ES$^+$ m/z=596.3; Rt: 2.09 min, method B.

Preparation of 28

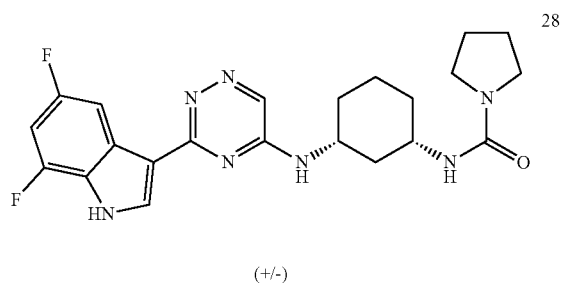 [SMILES: O=C(N[C@H]1CCC[C@@H](Nc2cnnc(-c3c[nH]c4c(F)cc(F)cc34)n2)C1)N1CCCC1]

28

(+/-)

Compound 28 was prepared according to the methods to prepare 25. $^1$H NMR (400 MHz, DMSO-d$_6$) δ ppm 1.09-1.36 (m, 3H) 1.44 (m, 1H) 1.73-1.86 (m, 2H) 1.73-1.86 (m, 4H) 2.08 (m, 2H) 3.14-3.25 (m, 4H) 3.56-3.66 (m, 1H) 3.93-4.04 (m, 1H) 5.82 (m, 1H) 6.99-7.07 (m, 1H) 7.99 (d, J=9.9 Hz, 2H) 8.27 (s, 2H). LC-MS ES$^+$ m/z=442.4; Rt: 1.62 min, method B.

Preparation of 29

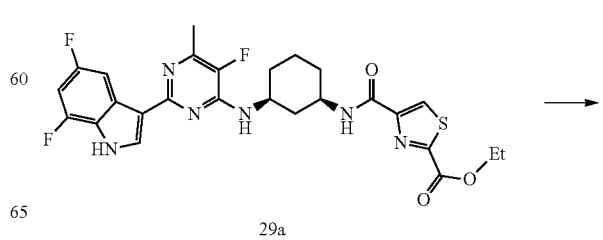

29a

29

-continued

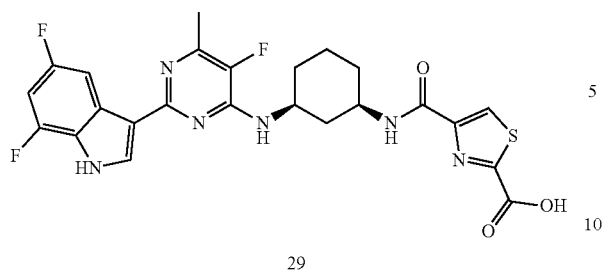

29

29 was prepared using methods analogous to those described in the experimental section with the exception that the final step required an ester hydrolysis using the following procedure. In a round bottom flask containing 29a and methanol (2.5 mL) was added NaOCH$_3$ (1.55 mL, 25 wt. % in methanol) and the mixture was stirred at room temperature for 4 hours under inert atmosphere. The organic layer was concentrated under vacuum and the mixture was purified by reverse phase chromatography. (start 70%[25 mM NH$_4$HCO$_3$]–30%[ACN: CH$_3$OH 1:1] and finished 27% [25 mM NH$_4$HCO$_3$]-73% [ACN: CH$_3$OH 1:1]).

Preparation of 30

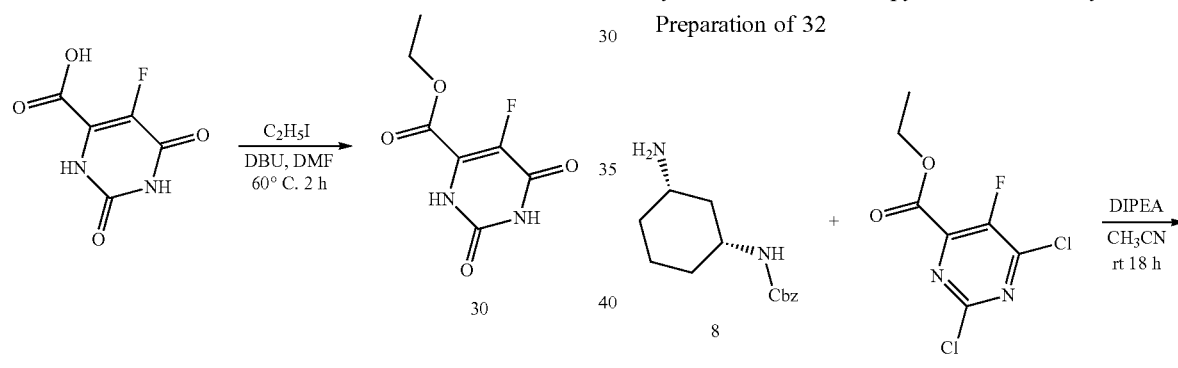

30

DBU (2.58 mL, 17.2 mmol) was added to a solution of 5-fluoroorotic acid (3 g, 17.2 mmol) in DMF (10 mL). After stirring for 30 minutes, iodoethane (2.69 g, 17.2 mmol) was added to the solution and the mixture was heated at 60° C. for 2 hours. Water (100 ml) was added to the mixture, and the precipitate was collected by filtration, washed with water, and dried to give 30, ethyl 5-fluoroorotate. LC-MS ES$^-$ m/z=200.9; Rt: 0.91 min, method D.

Preparation of 31

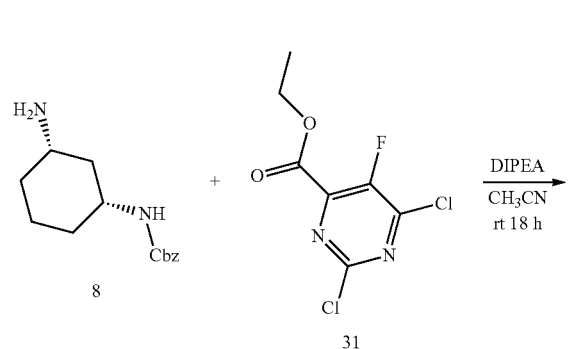

30

30

-continued

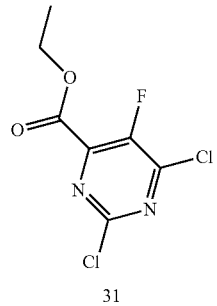

31

Ethyl 5-fluoroorotate 30 (2.13 g, 10.54 mmol) was added to a mixture of N,N-diethylaniline (1.09 mL, 7.16 mmol) and POCl$_3$ (2.64 mL, 28.45 mmol) at 90° C., and the mixture was heated to reflux for 4 hours. The solution was poured into ice water, and then sodium bicarbonate was added to bring the mixture to pH 8. The reaction mixture was extracted with ethyl acetate and washed with 5% aqueous potassium bisulfate, and brine. The organic layer was dried over sodium sulfate and concentrated in vacuo. The crude was purified by silica gel column chromatography using a n-heptane to n-heptane/EtOAc: 8/2 gradient. The desired fractions were pooled and evaporated to dryness to afford 31 ethyl 2,6-dichloro-5-fluoropyrimidine-4-carboxylate.

Preparation of 32

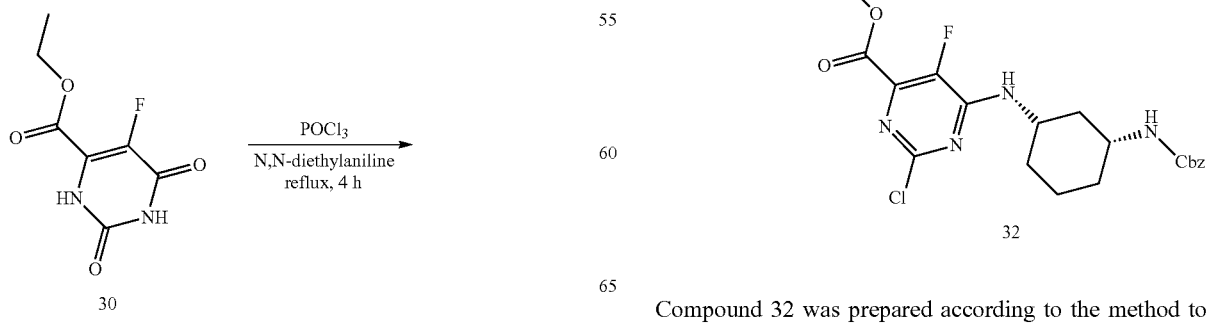

Compound 32 was prepared according to the method to prepare 9. LC-MS ES$^+$ m/z=451.2; Rt: 1.09 min, method A Preparation of 33

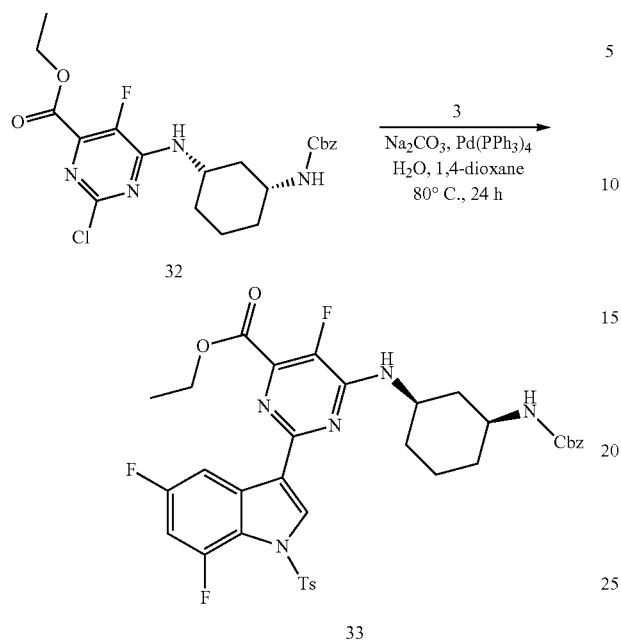

Compound 33 was prepared according to the method to prepare 10. LC-MS ES⁺ m/z=722.4; Rt: 2.56 min, method B Preparation of 34

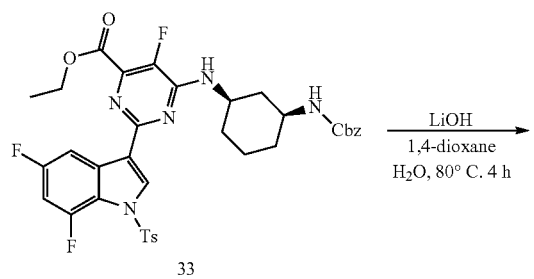

In a 250 mL flask 33 (1000 mg, 1.56 mmol) was stirred in 1,4-dioxane (45 mL) at rt, while a solution of LiOH (374 mg, 15.63 mmol) in water (5 mL) was added. The mixture was heated between 80 and 90° C. for 4 hours. The reaction mixture was neutralized with conc.

HCl and the solvent was removed under reduced pressure. The water layer was extracted with EtOAc, dried over MgSO₄, the solids were removed by filtration, and the solvent of the filtrate was removed under reduced pressure to afford 34. LC-MS ES⁺ m/z=540.2; Rt: 0.83 min, method A Preparation of 35

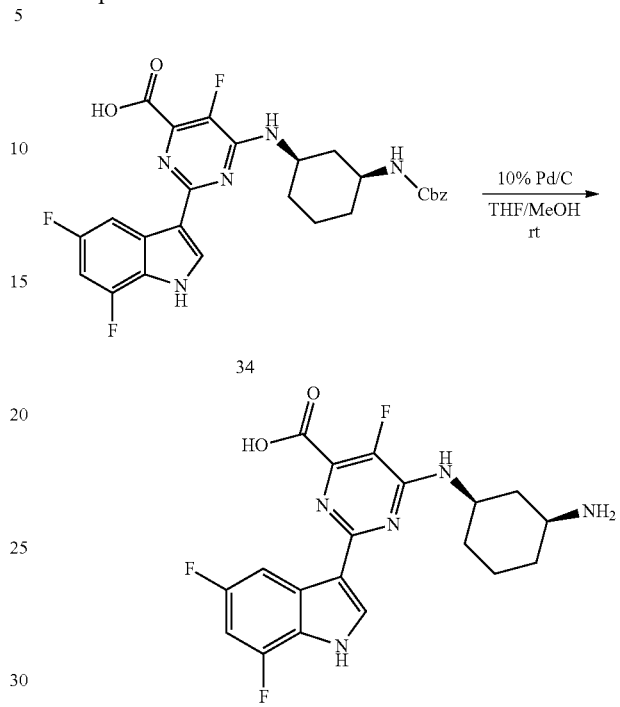

Pd/C (10%) (172 mg, 0.16 mmol) was added to a mixture of CH₃OH (15 mL) and THF (15 mL) under N₂ atmosphere. 34 (580 mg, 1.08 mmol) was added and the reaction mixture was stirred at 25° C. under a H₂ atmosphere until 1 eq. H₂ was consumed. The catalyst was removed by filtration over dicalite. The filtrate was concentrated under reduced pressure to afford 35. LC-MS ES⁺ m/z=406.3; Rt: 1.03 min, method B.

Preparation of 36

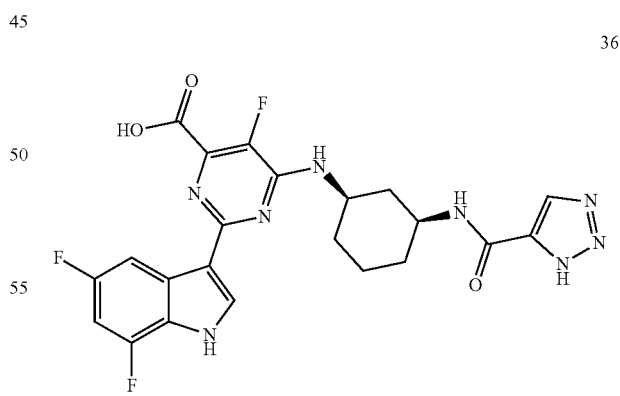

To a flask containing HBTU (140 mg, 0.37 mmol) and N,N-diisopropylethylamine (0.26 mL, 1.48 mmol) in DMF (10 mL) was added 1H-1,2,3-triazole-5-carboxylic acid (50 mg, 0.44 mmol) at room temperature. The mixture was stirred for 10 minutes under inert atmosphere, then 35 (150 mg, 0.37 mmol) was added and stirring continued at room temperature for 18h. The reaction mixture was concentrated and the crude was purified by preparatory HPLC (RP XBridge Prep C18 ODB-5 μm, 30×250 mm, mobile phase 0.25% aq. NH$_4$HCO$_3$, to acetonitrile). The best fractions were pooled and the solvents were removed under reduced pressure, yielding 36. LC-MS ES$^+$ m/z=501.2; Rt: 1.16 min, method A. $^1$H NMR (400 MHz, DMSO-d$_6$) δ ppm 1.22-1.68 (m, 1H) 1.80-1.91 (m, 2H) 1.95-2.07 (m, 1H) 2.12-2.23 (m, 1H) 3.87-4.08 (m, 2H) 4.10-4.30 (m, 1H) 6.89-7.12 (m, 1H) 7.50 (br s, 1H) 8.07 (m, 1H) 8.14 (s, 1H) 8.30 (br s, 1H) 8.38 (br d, 1H) 12.16 (br s, 1H).

sure ion source. It is within the knowledge of the skilled person to set the tune parameters (e.g. scanning range, dwell time, etc.) in order to obtain ions allowing the identification of the compound's nominal monoisotopic molecular weight (MW). Data acquisition was performed with appropriate software. Compounds are described by their experimental retention times (R$_t$) and ions. If not specified differently in the table of data, the reported molecular ion corresponds to the [M+H]$^+$ (protonated molecule) and/or [M−H]$^−$ (deprotonated molecule). In case the compound was not directly

TABLE 1

Compounds of formula (I) and corresponding analytical data. Compounds were prepared according to the methods described above or analogous procedures thereof.

| Cmpnd# | STRUCTURE | $^1$H NMR | Rt (min) | LC Method | LC-MS Mass Found [M + H]$^+$ | MP |
|---|---|---|---|---|---|---|
| 14 | [α]$_D^{23}$ −202.3° (c 0.14, CH$_3$OH) | $^1$H NMR (300 MHz, methanol-d$_4$) δ ppm 1.21-1.53 (m, 3 H) 1.55-1.73 (m, 1 H) 1.90-2.10 (m, 2 H) 2.16-2.30 (m, 1 H) 2.37 (s, 1 H) 2.33-2.42 (m, 3 H) 3.90 (s, 3 H) 4.00-4.14 (m, 1 1-1) 4.21-4.33 (m, 1 H) 6.74-6.83 (m, 1 H) 7.88 (s, 1 H) 8.04 (s, 1 H) 8.00-8.08 (m, 1 H) 8.09 (s, 1 H) | 2.28 | C | 483.9 | >300 |
| 15 | [α]$_D^{23}$ −255.1° (c 0.08, CH$_3$OH) | $^1$H NMR (300 MHz, methanol-d$_4$) δ ppm 1.28-1.52 (m, 2 H) 1.54-1.75 (m, 2 H) 1.93-2.15 (m, 2 H) 2.19-2.31 (m, 1 H) 2.34-2.45 (m, 1 H) 2.37 (s, 3 H) 4.08-4.19 (m, 1 H) 4.24-4.35 (m, 1 H) 6.75-6.84 (m, 1 H) 8.07 (s, 1 H) 8.03-8.11 (m, 1 H) 8.20 (s, 1 H) | 2.29 | C | 470.9 | >300 |
| 29 | [α]$_D^{23}$ −159.3° (c 0.12, DMF) | $^1$H NMR (300 MHz, DMSO-d$_6$) δ ppm 1.23-1.65 (m, 4 H) 1.86 (m, 2 H) 1.98-2.09 (m, 1 H) 2.13-2.25 (m, 1 H) 2.32 (d, J = 2.6 Hz, 3 H) 3.92-4.06 (m, 1 H) 4.09-4.23 (m, 1 H) 6.99-7.09 (m, 1 H) 7.35 (bm, 1 H) 8.05 (m, 1 H) 8.12 (d, J = 2.6 Hz, 1 H) 8.25 (m, 1 H) 8.46 (s, 1 H) 12.16 (br s, 1 H) | 2.25 | C | 531.1 | 263.2 |

Rt = retention time;
MP = melting point in ° C.

The High Performance Liquid Chromatography (HPLC) measurement was performed using a LC pump, a diode-array (DAD) or a UV detector and a column as specified in the respective methods. If necessary, additional detectors were included (see table of methods below).

Flow from the column was brought to the mass spectrometer (MS) which was configured with an atmospheric presionizable the type of adduct is specified (i.e. [M+NH$_4$]$^+$, [M+HCOO]$^−$, etc.). For molecules with multiple isotopic patterns (Br, Cl, etc), the reported value is the one obtained for the lowest isotope mass. All results were obtained with experimental uncertainties that are commonly associated with the method used.

| Method code | Instrument | Column | Mobile phase | Gradient | Flow Column T (° C.) | Run time (min) |
|---|---|---|---|---|---|---|
| A | Waters: Acquity® UPLC®-DAD and SQD | Waters: BEH C18 (1.7 µm, 2.1*50 mm) | A: 10 mM $CH_3COONH_4$ in 95% $H_2O$ + 5% $CH_3CN$ B: $CH_3CN$ | From 95% A to 5% A in 1.3 min, held for 0.7 min. | 0.8 55 | 2 |
| B | Waters: Acquity® UPLC®-DAD and SQD | Waters: HSS T3 (1.8 µm, 2.1*100 mm) | A: 10 mM $CH_3COONH_4$ in 95% $H_2O$ + 5% $CH_3CN$ B: $CH_3CN$ | From 100% A to 5% A in 2.10 min, to 0% A in 0.90 min, to 5% A in 0.5 min | 0.7 55 | 3.5 |
| C | Agilent 1100 -DAD-MSD G1956A | YMC-pack ODS-AQ C18 (50 × 4.6 mm, 3 µm) | A: 0.1% HCOOH in $H_2O$ B: $CH_3CN$ | From 95% A to 5% A in 4.8 min, held for 1.0 min, to 95% A in 0.2 min. | 2.6 35 | 6.0 |
| D | Waters: Acquity® UPLC® - DAD and SQD | Waters: HSS T3 (1.8 µm, 2.1*100 mm) | A: 10 mM $CH_3COONH_4$ in 95% H2O + 5% $CH_3CN$ B: CH3CN | From 100% A to 5% A in 2.10 min, to 0% A in 0.90 min, to 5% A in 0.5 min | 0.8 40 | 3.5 |
| E | Agilent 1290 Infinity DAD LC/MS G6110A | Phenomenex Kinetex C18 (50 × 2.1 mm, 1.7 µm) | A: 0.1% HCOOH in $H_2O$ B: $CH_3CN$ | From 90% A to 10% A in 1.5 min, held for 0.4 min, to 90% A in 0.1 min. | 1.5 60 | 2.0 |
| F | Agilent 1260 Infinity (Quat. Pump) DAD LC/MS G6120 (G1948B) | Thermo Scientific Accucore C18 (50 × 4.6 mm, 2.6 µm) | A: 0.1% HCOOH in $H_2O$ B: CH3CN | From 90% A to 10% A in 1.5 min, held for 0.9 min, to 95% A in 0.1 min. | 3.0 30 | 3.0 |

"SQD" Single Quadrupole Detector, "RT" room temperature, "BEH" bridged ethylsiloxane/silica hybrid, "HSS" High Strength Silica, "DAD" Diode Array Detector. Flow expressed in mL/min; column temperature (T) in ° C.; Run time in minutes.

Biological Activity of Compounds of Formula (I)

The in vitro antiviral activity of the compounds was determined using a cell-based antiviral assay. In this assay, the cytopathic effect (CPE) in Madin-Darby canine kidney (MDCK) cells infected by influenza virus A/Taiwan/1/86 (H1N1) was monitored in the presence or absence of the compounds. White 384-well microtiter assay plates (Greiner) were filled via acoustic drop ejection using the echo liquid handler (Labcyte, Sunnyvale, Calif.). Two hundred nanoliter of compound stock solutions (100% DMSO) were transferred to the assay plates. MDCK cells were dispensed to the plate at final density of 25,000 or 6,000 cells/well. Then Influenza A/Taiwan/1/86 (H1N1) virus was added at a multiplicity of infection of 0.001 or 0.01, respectively. The wells contain 0.5% DMSO per volume. Virus- and mock-infected controls were included in each test. The plates were incubated at 37° C. in 5% $CO_2$. Three days post-virus exposure, the cytopathic effect was quantified by measuring the reduction in ATP levels using the ATPlite™ kit (PerkinElmer, Zaventem, Belgium) according to the manufacturer's instructions. The $IC_{50}$ was defined as the 50% inhibitory concentration. In parallel, compounds were incubated for three days in white 384-well microtiter plates and the in vitro cytotoxicity of compounds in MDCK cells was determined by measuring the ATP content of the cells using the ATPlite™ kit (PerkinElmer, Zaventem, Belgium) according to the manufacturer's instructions. Cytotoxicity was reported as $CC_{50}$, the concentration that causes a 50% reduction in cell viability.

TABLE 2

Biological Activity of compounds of formula (I).

| Compound # | Influenza A/Taiwan/1/86 $IC_{50}$ µM | TOX MDCK $CC_{50}$ µM |
|---|---|---|
| 6 | 0.130 | >5 |
| 13 | 0.001 | 10.4 |
| 14 | 0.002 | >25 |
| 15 | 0.0002 | 3.4 |
| 21 | 0.001 | >25 |
| 25 | 0.026 | 9.7 |
| 28 | 0.008 | 15.5 |
| 29 | 0.002 | 21 |
| 36 | 0.007 | >25 |

The invention claimed is:
1. A compound of formula (I)

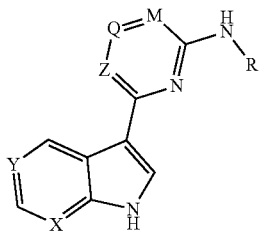

or a stereoisomeric form thereof, or a pharmaceutically acceptable salt thereof, wherein:
(a) X is N and Y is N; or
(b) X is C substituted by F and Y is C substituted by —F, —CH₃, or —CN;
(1) Z is N, Q is —C—CH₃, —C—COOH, —C—CF₃, —CH-cyclopropyl, —CH₂R₁,
or —CONR₁R₁, and M is CF;
wherein each R₁ is independently selected from hydrogen, halogen, cyano, oxo, alkyl, hydroxyl, and amino; or
(2) Z is N, Q is N, and M is CH; or
(3) Z is C, Q is N, and M is CH; and
R is C₃₋₈ cycloalkyl substituted by (i) carboxylic acid or (ii)—NH—C(O)—C₃₋₆ heterocycle
optionally substituted by C₁₋₆ alkyl or —COOH.

2. A compound according to claim 1 having the structural formula

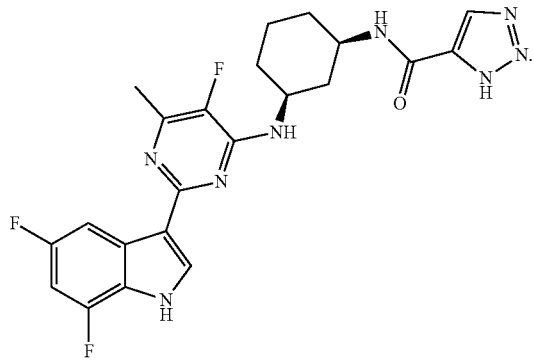 [SMILES: Cc1nc(-c2c[nH]c3c(F)cc(F)cc23)nc(N[C@H]2CCC[C@@H](NC(=O)c3cnn[nH]3)C2)c1F]

or a pharmaceutically acceptable salt thereof.

3. A compound selected from the group consisting of:

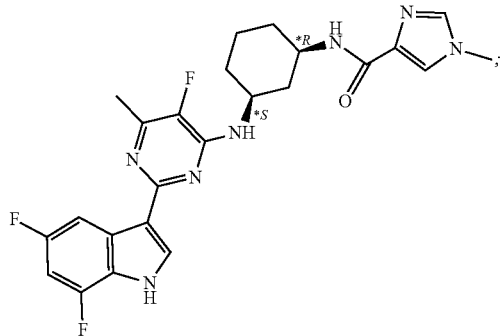

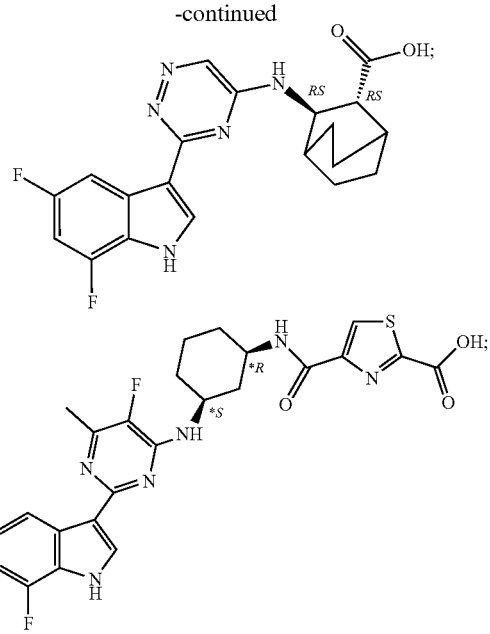

and

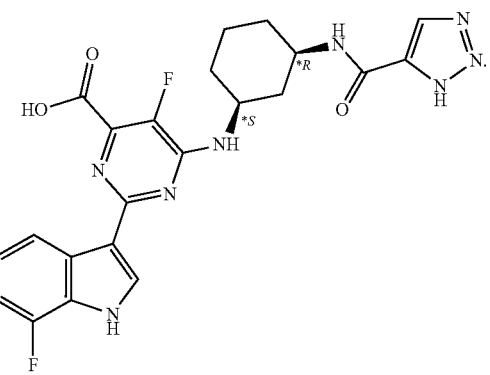

and pharmaceutically acceptable salts thereof.

4. A pharmaceutical composition comprising a compound of claim 1 together with one or more pharmaceutically acceptable excipients, diluents or carriers.

5. A method of treating influenza infection in a patient comprising administering to the patient a compound represented by the following structural formula (I)

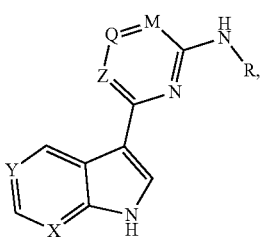

or a stereoisomeric form thereof, or a pharmaceutically acceptable salt thereof, wherein:
(a) X is N and Y is N; or
(b) X is C substituted by —F and Y is C substituted by —F, —Cl, —CH₃, or —CN;

(1) Z is N, Q is —C—CH$_3$, —C—COOH, —C—CF$_3$, —CH-cyclopropyl, —CH$_2$R$_1$, or —CONR$_1$R$_1$, and M is CF;
   wherein each R$_1$ is independently selected from hydrogen, halogen, cyano, oxo, alkyl, hydroxyl, and amino; or
(2) Z is N, Q is N, and M is CH; or
(3) Z is C, Q is N, and M is CH; and
R is C$_{3-8}$ cycloalkyl substituted by (i) carboxylic acid or (ii) —NH—C(O)—C$_{3-6}$ heterocycle optionally substituted by C$_{1-6}$ alkyl or —COOH.

6. The method of claim 5, further comprising co-administering an additional therapeutic agent.

7. The method of claim 6, wherein the additional therapeutic agent is an antiviral agent or an influenza vaccine, or both.

8. The method of claim 7, wherein the additional therapeutic agent is an antiviral agent.

9. The method of claim 5, wherein the compound or the stereoisomeric form thereof, or the pharmaceutically acceptable salt thereof, is administered to the patient in a pharmaceutical composition together with one or more pharmaceutically acceptable excipients, diluents or carriers.

10. The method of claim 5, wherein the compound is represented by the following structural formula (I):

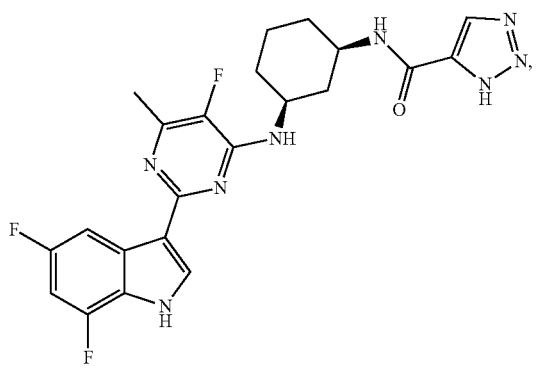

or a stereoisomeric form thereof, or a pharmaceutically acceptable salt thereof.

* * * * *